(12) United States Patent
Toepfer

(10) Patent No.: US 11,452,491 B2
(45) Date of Patent: Sep. 27, 2022

(54) AUTOMATIC EXPOSURE CONTROL SETUP

(71) Applicant: CARESTREAM HEALTH, INC., Rochester, NY (US)

(72) Inventor: Karin Toepfer, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 22 days.

(21) Appl. No.: 17/023,448

(22) Filed: Sep. 17, 2020

(65) Prior Publication Data

US 2021/0000440 A1    Jan. 7, 2021

Related U.S. Application Data

(63) Continuation of application No. 15/963,135, filed on Apr. 26, 2018, now abandoned.

(60) Provisional application No. 62/507,290, filed on May 17, 2017.

(51) Int. Cl.
*A61B 6/00* (2006.01)
*A61B 6/03* (2006.01)
*A61B 6/04* (2006.01)

(52) U.S. Cl.
CPC .............. *A61B 6/544* (2013.01); *A61B 6/032* (2013.01); *A61B 6/04* (2013.01); *A61B 6/4085* (2013.01); *A61B 6/4405* (2013.01); *A61B 6/463* (2013.01); *A61B 6/465* (2013.01); *A61B 6/50* (2013.01); *A61B 6/5205* (2013.01); *A61B 6/5223* (2013.01); *A61B 6/5258* (2013.01);
(Continued)

(58) Field of Classification Search
CPC .. A61B 6/00; A61B 6/03; A61B 6/544; A61B 6/5258; A61B 6/488; A61B 6/4085; A61B 6/463; A61B 6/032; A61B 6/542; A61B 6/54; A61B 6/545; A61B 6/10; A61B 6/04; A61B 6/5223; A61B 6/5205; A61B 6/50; A61B 6/4405; A61B 6/465
See application file for complete search history.

(56) References Cited

U.S. PATENT DOCUMENTS

| | | |
|---|---|---|
| 5,270,926 A | 12/1993 | Tam |
| 5,999,587 A | 12/1999 | Ning et al. |
| 6,639,999 B1 | 10/2003 | Cookingham et al. |

(Continued)

FOREIGN PATENT DOCUMENTS

WO    2007/114470    10/2007

OTHER PUBLICATIONS

John A. Carrino et al., "Dedicated Cone-Beam CT System for Extremity Imaging", *Radiology*. Mar. 2014; 270(3): pp. 816-824.

(Continued)

*Primary Examiner* — Jurie Yun

(57) ABSTRACT

A method for exposure control setup for a volume radiographic imaging apparatus obtains a reconstructed image volume of a subject acquired from the imaging apparatus using a set of x-ray technique settings. An image slice from the reconstructed image volume displays in at least a first rendering having a first corresponding noise factor and a second rendering having a second corresponding noise factor, different from the first noise factor. An operator instruction selects one of the at least first and second renderings and stores the corresponding noise factor for the set of x-ray technique settings. An automatic exposure control of the imaging apparatus is configured according to the stored noise factor.

10 Claims, 14 Drawing Sheets

(52) U.S. Cl.
CPC .............. *A61B 6/542* (2013.01); *A61B 6/545* (2013.01); *A61B 6/488* (2013.01)

(56) References Cited

U.S. PATENT DOCUMENTS

| | | |
|---|---|---|
| 6,658,139 B1 | 12/2003 | Cookingham et al. |
| 7,480,365 B1 | 1/2009 | Topfer et al. |
| 7,970,192 B2 * | 6/2011 | Boeing .................. A61B 6/032 382/131 |
| 8,903,037 B2 | 12/2014 | Yu et al. |
| 9,717,467 B2 | 8/2017 | Litzenberger et al. |
| 10,068,318 B2 | 9/2018 | Dzyubak et al. |
| 2005/0008115 A1 | 1/2005 | Tsukagoshi |
| 2013/0051527 A1 | 2/2013 | Sakaguchi et al. |
| 2014/0037178 A1 | 2/2014 | Park |
| 2015/0178917 A1 | 6/2015 | Yang et al. |
| 2015/0359501 A1 | 12/2015 | Eronen et al. |

OTHER PUBLICATIONS

Paper, "Dose Considerations for Onsight 3D Extremity System", J. Yorkston, K. Toepfer, Carestream OnSight 3D Extremity System, 2017, 3 pages.

McKenney et al , "Methods for CT Automatic Exposure Control Protocol Translation Between Scanner Platforms" in *J. Am. Coll. Radiol.* Mar. 2014, pp. 285-291.

Cao Q. et al., "Multiresolution Iterative Reconstruction in High-Resolution Extremity Cone-Beam CT", *Phys Med Biol.* Oct. 21, 2016;61(20): 7263-7281, pp. 1-27.

European Search Report dated Dec. 10, 2018 for European Patent Application No. 18 172 637.3, 2 pages.

\* cited by examiner

AUTOMATIC EXPOSURE CONTROL SETUP

CROSS REFERENCE TO RELATED APPLICATIONS

This patent application is a continuation of U.S. patent application Ser. No. 15/963,135, filed on Apr. 26, 2018, entitled "AUTOMATIC EXPOSURE CONTROL SETUP", in the name of Toepfer, which claims the benefit of U.S. Provisional Application U.S. Ser. No. 62/507,290, filed on May 17, 2017, entitled "TOOL FOR AEC SETUP IN CT IMAGING", in the name of Toepfer, which is hereby incorporated by reference herein in its entirety.

TECHNICAL FIELD

The disclosure relates generally to the field of computed tomography (CT). More specifically, the disclosure relates to a tool for AEC (automatic exposure control) setup in CT and/or cone beam computed tomography (CBCT) imaging.

BACKGROUND

3-D volume imaging has proved to be a diagnostic tool that offers advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Cone beam computed tomography (CBCT) or cone beam CT technology is one type of diagnostic tool for providing 3-D volume images. Cone beam CT systems capture volumetric data sets by using a high frame-rate digital radiography (DR) detector and an x-ray source, typically affixed to a gantry that rotates about the object to be imaged, directing, from various points along its orbit around the subject, a divergent cone beam of x-rays toward the subject. The CBCT system captures projections throughout the rotation such as, for example, one 2-D projection image at every degree of rotation. The projections are then reconstructed into a 3-D volume image using various techniques. Among well known methods for reconstructing the 3-D volume image from the 2-D image data are filtered back-projection approaches.

CBCT imaging is a variant of more traditional computed tomography (CT) imaging, with some notable differences from the CT modality in operation and radiation delivery.

CT scanning is shown schematically in FIG. 1A. As shown schematically in FIG. 1A, the CT scan pattern about the patient is typically helical. Using a high-output x-ray tube 12, CT scanning images a volume one narrow slice at a time, using an x-ray fan beam from a source and detector 14 hardware so that the scanning beam effectively revolves about the patient one or more times for obtaining the needed volume. The patient is moved through the CT scanning hardware as it revolves. Most modern CT systems are referred to as MDCT (Multi-Detector CT) systems. In MDCT, a two-dimensional array of detector elements replaces the linear array of detector elements used in typical conventional and helical CT scanners, resulting in faster throughput. In traditional CT reconstruction, the z-axis spatial resolution (the spatial resolution in the direction of motion of the patient) is determined by the speed of translation of the patient through the imaging X-ray fan, coupled with the speed of rotation of the X-ray source around the patient. Special mechanical design features, e.g., high-speed "slip ring" technology, are required to support fast motion of the x-ray assembly. CT systems are typically expensive, have a large foot print, and can generally be found in large hospitals and imaging centers.

CBCT scanning is shown schematically in FIG. 1B. As shown schematically in FIG. 1B. CBCT has a radiation source 22 that provides a larger cone beam and a detector 24 and acquires the volume data in a single rotation around the patient. CBCT scanning can use available low-power fluoroscopy tubes to generate a cone-shaped X-ray beam and high-speed flat panel detectors based on hydrogenated amorphous silicon (a-Si:H). This allows CBCT to employ a simplified system design, which has isotropic spatial resolution in the reconstructed 3-D volumes as an additional benefit. The simplified design leads to lower cost and a much smaller footprint compared with traditional scanners, making these systems suitable for point-of-care imaging. For these reasons. CBCT systems extend the use of high-quality three-dimensional imaging to a much wider audience than previously served by traditional CT.

Recently, a range of newly specialized volumetric imaging systems has become available. CBCT systems have been designed for specific anatomical locations such as dental, ENT (Ear, Nose and Throat), orthopedic, and breast imaging as well as for image guidance in radiation therapy and intra-operative applications. These dedicated systems enable new applications and enhance patient comfort. For example, extremity imaging can be performed by CBCT systems having a small footprint, ergonomically designed to allow imaging in weight-bearing as well as non-weight-bearing postures, and providing isotropic resolution, with optimized design and image processing.

Reference is made to John A. Carrino et al., "DEDICATED CONE-BEAM CT SYSTEM FOR EXTREMITY IMAGING", *Radiology*. March 2014; 270(3): 816-824, incorporated herein by reference in its entirety.

There is a need with selecting the appropriate dose levels for CBCT imaging. Applicants have recognized that there is a need for an operator interface utility that relates patient dose to adequate image quality for a diagnostic task, for example in terms of noise level, and assists the operator in the selection of automatic exposure control settings.

SUMMARY

An object of the present disclosure is to address the need for setting up the automatic exposure control for CBCT and CT imaging to achieve the desired balance of low patient dose and adequate diagnostic image quality. Methods of the present disclosure can have particular value with three-dimensional X-ray imaging of specific anatomical locations, e.g., patient extremities, such as arms, hands, legs, and feet, breast, and head and dental and ENT imaging.

These objects are given only by way of illustrative example, and such objects may be exemplary of one or more embodiments of the invention. Other desirable objectives and advantages inherently achieved may occur or become apparent to those skilled in the art. The invention is defined by the appended claims.

According to one aspect of the disclosure, there is provided a method for exposure control setup for a volume radiographic imaging apparatus, the method comprising: obtaining a reconstructed image volume of a subject acquired from the imaging apparatus using a set of x-ray technique settings; displaying an image slice from the reconstructed image volume in at least a first rendering having a first corresponding noise factor and a second rendering having a second corresponding noise factor, different from the first noise factor; accepting an operator instruction that selects one of the at least first and second renderings and storing the corresponding noise factor for the set of x-ray technique settings; and configuring an automatic exposure control of the imaging apparatus according to the stored noise factor.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

Figure 1B:
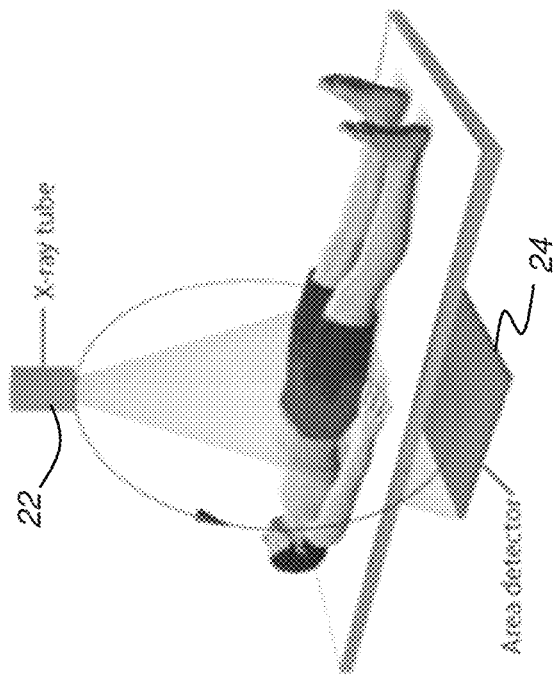
FIG. 1B is a schematic diagram showing a cone-beam computed tomography apparatus.

The following is a detailed description of the embodiments of the disclosure, reference being made to the drawings in which the same reference numerals identify the same elements of structure in each of the several figures.

In the following description, a preferred embodiment of the present disclosure will be described as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present disclosure. Other aspects of such algorithms and systems, and hardware and/or software for producing and otherwise processing the image signals involved therewith, not specifically shown or described herein, may be selected from such systems, algorithms, components, and elements known in the art.

In the context of the present disclosure, the term "extremity" has its meaning as conventionally understood in diagnostic imaging parlance, referring to knees, legs, ankles, fingers, hands, wrists, elbows, arms, and shoulders and any other anatomical extremity. The term "subject" is used to describe the extremity or other anatomy of the patient, phantom, or cadaver that is imaged, such as the "subject leg", for example.

The term "actuable" has its conventional meaning, relating to a device or component that is capable of effecting an action in response to a stimulus, such as in response to an electrical signal, for example.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be data communication, power, or energy level signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, "volume image content" describes the reconstructed 3-D image data for an imaged subject, generally stored as a set of voxels. Image display utilities use the volume image content in order to display features within the volume, rendered by selecting specific voxels that represent the volume content for a particular slice or view of the imaged subject. Thus, volume image content is the body of resource information that is obtained from a CT, CBCT, MDCT, tomosynthesis, or other volume imaging reconstruction process and that can be used to generate depth visualizations of the imaged subject. The radiographic imaging apparatus defines a volume between the radiation source and the detector. For 3-D imaging apparatus, the source and detector orbit the volume for anatomy imaging.

CBCT imaging apparatus and the imaging algorithms used to obtain 3-D volume images using such systems are well known in the diagnostic imaging art and are, therefore, not described in detail in the present application. Some exemplary algorithms and approaches for forming 3-D volume images from the source 2-D projection images that are obtained in operation of the CBCT imaging apparatus can be found, for example: U.S. Pat. No. 5,999,587 entitled "METHOD OF AND SYSTEM FOR CONE-BEAM TOMOGRAPHY RECONSTRUCTION" (Ning); U.S. Pat. No. 5,270,926 entitled "METHOD AND APPARATUS FOR RECONSTRUCTING A THREE-DIMENSIONAL COMPUTERIZED TOMOGRAPHY (CT) IMAGE OF AN OBJECT FROM INCOMPLETE CONE BEAM DATA" (Tam); and U.S. 2015/0178917 entitled "METAL ARTIFACTS REDUCTION FOR CONE BEAM CT USING IMAGE STACKING" (Yang), all of these references are incorporated herein in their entirety by reference.

In typical applications, a computer or other type of dedicated logic processor for obtaining, processing, and storing image data is part of the CBCT system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice the method according to the present disclosure.

An aspect of 3-D X-ray imaging is the increase in radiation dose as compared with 2-D procedures, for example 2-D radiographs of chest and extremities.

To accurately measure the biological significance of exposure to X-rays, the International Commission on Radiological Protection (ICRP) has defined Effective Dose as the metric for evaluation of the biological impact of exposure to ionizing radiation. An Effective Dose calculation incorporates the X-ray energy absorbed by different types of biological tissue, the fraction of the patient's anatomy that is being imaged, and the specific radiation-sensitivities of those tissues. This measure is intended to reflect the significance of the biological impact of the radiation used for the given imaging study. The unit for effective dose is micro Sievert (pSv). According to a recent compilation of data on effective dose, daily background radiation amounts to 17 pSv, a 2-D chest radiograph is somewhat higher at 20 to 100 pSv, a CBCT scan of an extremity is comparable at 5 to 40 pSv and a MDCT head scan is at 2000 pSv, more than 100 times the daily background radiation. This set of numbers illustrates the need for dose reduction in 3-D X-ray imaging.

Reference is made to the paper, "DOSE CONSIDERATIONS FOR ONSIGHT 3D EXTREMITY SYSTEM", J. Yorkston, K. Toepfer, Carestream Health, Inc., 2017, incorporated herein by reference in its entirety.

Manufacturers of traditional MDCT systems have addressed the need to achieve adequate diagnostic image quality at the lowest possible dose with a number of different methods. Some MDCT systems have automatic exposure control (AEC) to adapt the imaging techniques in terms of peak kilo-voltage (kVp), tube current (mA) and slice scan time to the size and anatomy of the patient. Moreover, some systems have tube current modulation to change the tube current of individual slices according to the anatomy. Additional dose reductions can be achieved with bowtie filters and advanced 3-D image reconstruction protocols which help to reduce the image noise.

Exposure, and consequently radiation dose, depend in part on tube current and slice scan time, typically expressed in units of mAs, as a product of current and time. Increasing the mAs (by increasing tube current or extending the slice scan time) increases the dose proportionally: a level of 300 mAs delivers twice the dose of 150 mAs. Thus, CT radiation dose is often expressed as dose per mAs.

The dose in CBCT systems can be lower than in traditional MDCT systems because design and image processing are optimized for the imaged anatomy. However, achieving low dose in combination with adequate diagnostic image quality is viewed by some practitioners to be important. Design features can include AEC, bowtie filters, collimation and optimized model-based iterative 3-D image reconstruction.

One dose control feature for MDCT and CBCT is the AEC (automatic exposure control) function. The AEC can be set up to provide the desired/preferred trade-off between low dose and the required diagnostic image quality.

The information contained in the 3-D reconstructed image volumes is typically standardized for CT and CBCT. Both technologies attempt to reconstruct the 3-D material distribution in the body (i.e., different tissues and organs, e.g., bone, muscle, adipose tissue, lung, liver, blood, and the like) displayed at different gray levels. The materials are quantified in terms of the linear attenuation coefficient of the X-rays. The Hounsfield unit provides a common scale for CT imaging. The Hounsfield unit (HU) scale is a linear transformation of the original linear attenuation coefficient measurement into one in which the radiodensity of distilled water at standard pressure and temperature (STP) is defined as zero Hounsfield units (HU), while the radiodensity of air at STP is defined as −1000 HU.

Regarding the AEC functionality, the exposure is usually controlled based on the X-ray technique (kVp, filtration), size of the anatomy, and a user-provided image quality factor.

Reference is made to U.S. Pat. No. 8,903,037 titled "SYSTEM AND METHOD FOR AUTOMATIC TUBE POTENTIAL SELECTION FOR DOSE REDUCTION IN MEDICAL IMAGING" (Yu), and US 2015/0359501 titled "SYSTEMS AND METHODS OF AUTOMATED DOSE CONTROL IN X-RAY IMAGING" (Eronen), both incorporated herein in their entirety by reference.

A metric used to characterize image quality in CT imaging is the noise factor, typically quantified as a measure of the noise in HU for a standard size reconstructed PMMA phantom (16 or 32 cm in diameter, or other sizes). Related image quality characteristics include a signal-to-noise ratio (variously abbreviated SN or SNR, for example, the ratio of the linear attenuation coefficient of the phantom material and the noise in terms of the linear attenuation coefficient), a contrast-to-noise ratio (abbreviated CNR), or some other proprietary measure of image quality. In X-ray imaging, polymethyl methacrylate (PMMA), also known as Plexiglas™, is frequently used as a representation of human tissue. These measures can be easily defined for CT and CBCT systems, and the definitions could even be identical for both types of systems. For quantum-limited systems, the noise level in the reconstructed images is in inverse proportion to the square root of the exposure level; the higher the exposure, the lower the perceptible image noise. Understanding this relationship promotes achieving suitable control of the exposure applied to the patient. SNR and CNR also determine the contrast resolution of the system, i.e., which difference in HU can be resolved (distinguished by the user) in the displayed images.

Because of inherent differences between CT and CBCT imaging, for example due to system geometry, the X-ray techniques used in terms of kVp, additional filtration and mAs, various additional design features to reduce dose, and differences in the sophistication of 3-D reconstruction algorithms, it can be difficult to compare the quality index between different systems.

Reference is made to the article by McKenney et al. entitled "METHODS FOR CT AUTOMATIC EXPOSURE CONTROL PROTOCOL TRANSLATION BETWEEN SCANNER PLATFORMS" in *J. Am. Coll. Radiol.* 2014 March, pp. 285-291, incorporated herein by reference. This article investigates the difficulties in translating exposure measurements and related noise index metrics between different CT scanner equipment from various manufacturers. Those skilled in the art can appreciate that the comparison of CT and CBCT systems is challenging because of the inherent differences between the two technologies discussed above.

CT and CBCT systems are available from various manufacturers, some of which apply different tools and techniques for interpreting and balancing noise factor and dose considerations. Even if practitioners at a site were familiar with one type of system, alternative systems can exhibit different response related to noise factors, complicating the job of making judicious decisions related to radiation dose for a particular procedure. For example, a site familiar with CT system imaging may find it difficult to adapt to CBCT imaging as it relates to noise factors, sharpness resolution along different axes, noise distribution within the 3-D volume, and other aspects of image quality that differ between the two technologies. In addition, differences in image reconstruction techniques, such as with iterative reconstruction, can add to the difficulty of making good decisions in the tradeoff between image quality and patient exposure. Similarly, practitioners who make the transition from 2-D to 3-D imaging may not be familiar with image quality metrics for the new 3-D technology.

Quantification of image quality has been developed for pictorial imaging, i.e., photography with visible light, using image quality rulers.

Reference is made to U.S. Pat. No. 6,658,139 entitled "METHOD FOR ASSESSING OVERALL QUALITY OF IMAGES" (Cookingham), and U.S. Pat. No. 6,639,999 entitled "APPARATUS FOR ASSESSING OVERALL QUALITY OF HARDCOPY IMAGES" (Cookingham), both incorporated herein in their entirety by reference.

Image quality rulers depict various levels of a perceptual image quality attribute, for example sharpness or noise, in ascending or descending order. Usually, an image quality number is associated with each image, and the user can match the image quality of a test image with one of the image quality levels on the ruler. The user can interpolate between different image quality levels presented for more accurate results. The image quality attribute presented on the ruler, for example varying sharpness, can differ from the type of image quality degradation present in the test image, which, for example, may suffer from high noise. The instructions can emphasize comparison of overall image quality, and not any individual image quality attribute, of the ruler and the test image. Image quality rulers can be assembled for hardcopy and softcopy presentation. In one implementation, image quality rulers have perceptually equidistant steps of the depicted attribute, also referred to as just noticeable differences, or JNDs. Such perceptual calibration is usually performed in extensive psychophysical experiments using paired or other multiple-choice comparisons.

Applicants have recognized that image quality ruler technology can be adapted to setting up the AEC of different CT and CBCT systems for matched image quality, despite the sometimes different appearance of the reconstructed volumes. However. Applicants have recognized that there can be differences in the use of rulers for medical and pictorial imaging. Pictorial imaging usually strives for a high image quality given the available light. Medical imaging, in contrast, may consider/regard the trade-off between image quality and patient dose. The images for rulers in medical image quality assessment are preferably selected such that the user can assess which level of image quality is suitable and/or sufficient to perform the required diagnostic task. The image set could, for example, contain known disease features such as fractures in orthopedic imaging.

In more particularly understand the methods of the present disclosure and the problems addressed, it is instructive to review principles and terminology used for CBCT image capture and reconstruction.

Figure 2:
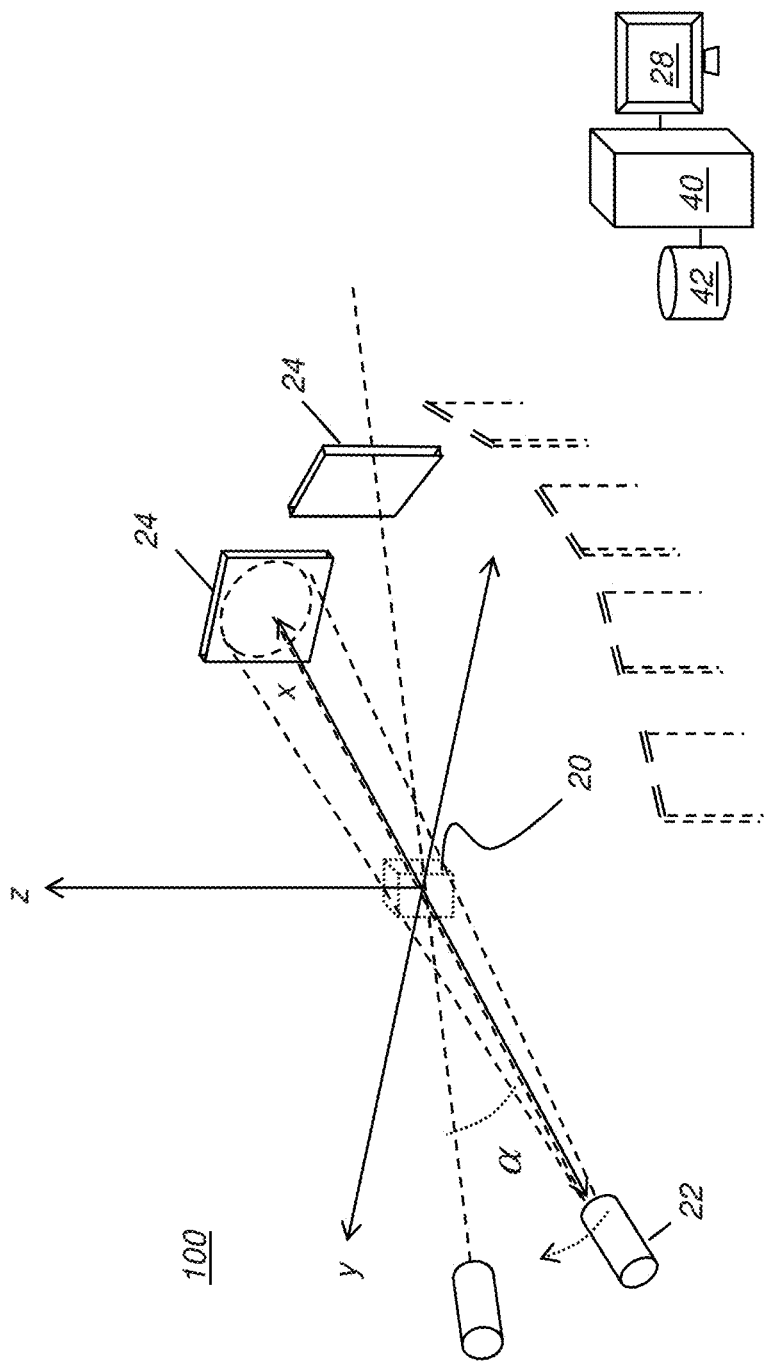
FIG. 2 is a block diagram schematic that shows how projection images are obtained.

Referring to the perspective view of FIG. 2, there is shown, in schematic form and using enlarged distances for clarity of description, the activity of a conventional CBCT extremity imaging apparatus 100 for acquiring the individual 2-D images that are used to form a 3-D volume image. A cone-beam radiation source 22 directs a cone of radiation toward a subject 20, such as a patient or other subject. A sequence of acquired 2-D projection images is obtained in rapid succession at varying angles about the subject, such as one image at each 1-degree angle increment in a 200-degree orbit. A digital radiography (DR) detector 24 is moved to different imaging positions about subject 20 in concert with corresponding orbital movement of radiation source 22.

FIG. 2 shows a representative sampling of DR detector 24 positions to illustrate how these acquired projection images are obtained relative to the position of subject 20 in an extremity imaging apparatus 100. Once the desired 2-D projection images are captured in this sequence, a suitable imaging algorithm, such as filtered back projection (FBP) or other advanced iterative reconstruction method (for example: Cao Q., Zbijewski W., Sisniega A., Yorkston J., Siewerdsen J. H., Stayman J. W., "MULTIRESOLUTION ITERATIVE RECONSTRUCTION IN HIGH-RESOLUTION EXTREMITY CONE-BEAM CT", *Phys Med Biol.* 2016 Oct. 21; 61(20):7263-7281, incorporated herein by reference it its entirety), is used for reconstruction of the 3-D volume image. Image acquisition and program execution for generating the reconstructed 3-D image are performed by a computer 40 or a networked group of computers 40 in image data signal communication with DR detectors 24. Image processing and storage is performed using a computer-accessible memory 42. The reconstructed 3-D volume image can be rendered for from a range of angles for presentation on a display 28.

Figure 3:
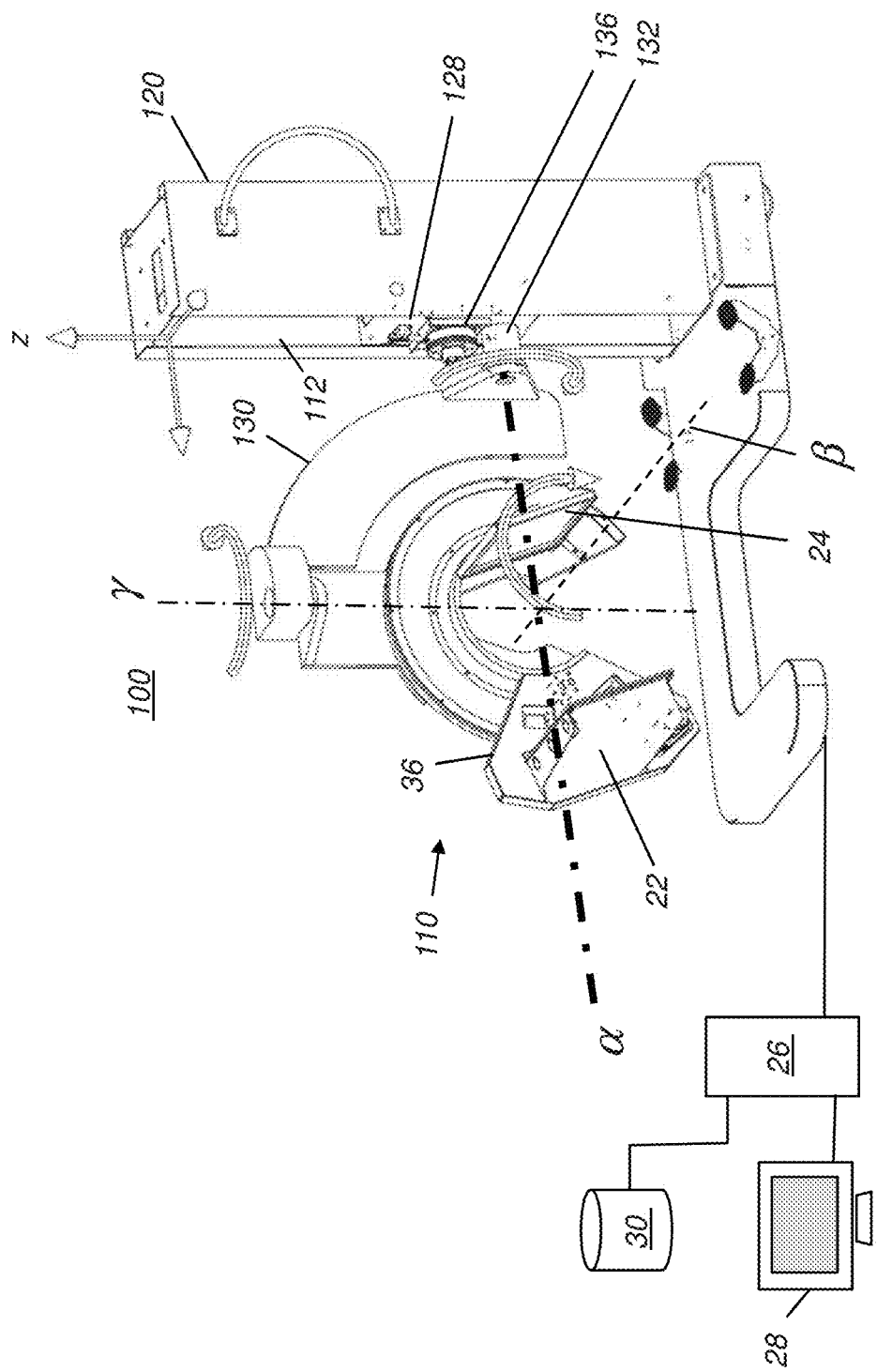
FIG. 3 is a perspective view of a CBCT imaging apparatus for extremity imaging.

Extremity imaging apparatus 100 in FIG. 3 provides the capability for configuration and for positioning of the patient in a suitable posture for imaging. Imaging apparatus 100 allows the advantages of CBCT imaging to be adaptable for use with a range of extremities, to obtain volume images under a suitable imaging modality, with the image extremity presented at a suitable orientation under both load-bearing and non-load-bearing conditions, and with the patient appropriately standing or seated.

FIG. 3 shows portions of the internal imaging and positioning mechanisms (for illustrative purposes, with covers removed) for a scanner 110 that allow imaging apparatus 100 the capability for imaging extremities with a variety of configurations. A description of imaging mechanics and features is provided, for example, in U.S. Pat. No. 9,717,467 entitled "EXTREMITY IMAGING APPARATUS FOR CONE BEAM COMPUTED TOMOGRAPHY" (Litzenberger), incorporated herein by reference in its entirety.

For an understanding of the context of the present disclosure, it is useful to describe some aspects of the design and operation of imaging apparatus 100 as they relate to how extremity images can be acquired.

Multiple axes allow the apparatus to provide scanning at various orientations, including horizontal scans, such as for legs and feet, and vertical scans, such as for arms, elbows, and hands. The patient/subject can be imaged in a variety of positions, including prone, sitting, and standing. The a-axis and the y-axis are non-parallel, allowing gimbaled action. According to an embodiment of the present disclosure as shown in FIG. 3, the a-axis and the y-axis are mutually orthogonal. In a one arrangement, the a-axis is substantially orthogonal to the z-axis. The intersection of the a-axis and the y-axis is offset from a support column 120 by a non-zero distance.

Considering the z-axis, FIG. 3 illustrates the achievement of vertical motion. Within support column 120, a vertical carriage translation element 128 is actuated to travel, for example, upwards or downwards along column 120 within a track 112 in a vertical/linear direction. Carriage translation element 128 has a support shaft 132 coupled to an actuator 136 for providing a-axis rotation to (forked or C-shaped) support arm 130. Support arm 130, shown only partially in FIG. 3 to allow a better view of underlying components, is coupled to support shaft 132. X-ray radiation source 22 and detector 24 are mounted on a rotatable gantry 36 for rotation about a scan or central axis, designated as the § axis. Axis 0 is orthogonal to the a-axis and the y-axis in the embodiment shown.

It can be appreciated that z-axis translation can be effected in a number of ways. Challenges addressed by the type of system that is used include handling the weight of support arm 130 and the imaging scanner 110 that support arm 130 supports. For stability and safety purposes, its weight may be a few hundred pounds. In addition, safety precautions are provided for handling conditions such as power loss, contact with the patient, or mechanical problems that hamper positioning movement or operation.

Other features of support column 120 for vertical translation may include built-in redundancy, with springs to absorb weight and impact, the load cell to sense a mechanical problem including obstruction by the patient, and manually operable brake mechanisms.

Still referring to FIG. 3, a computer or other type of control logic processor 26 is in signal communication with mechanical and electronic components of imaging apparatus 100 for acquiring the reflectance image content and generating surface contour information. A display 28 is in signal communication with control logic processor 26 for reporting results and providing an operator interface for control and viewing functions, as described in more detail subsequently. A memory 30 in signal communication with computer or control logic processor 26 stores image data as well as information related to examination types and pre-determined image acquisition techniques, properties of different views and other setup information.

Figure 4:
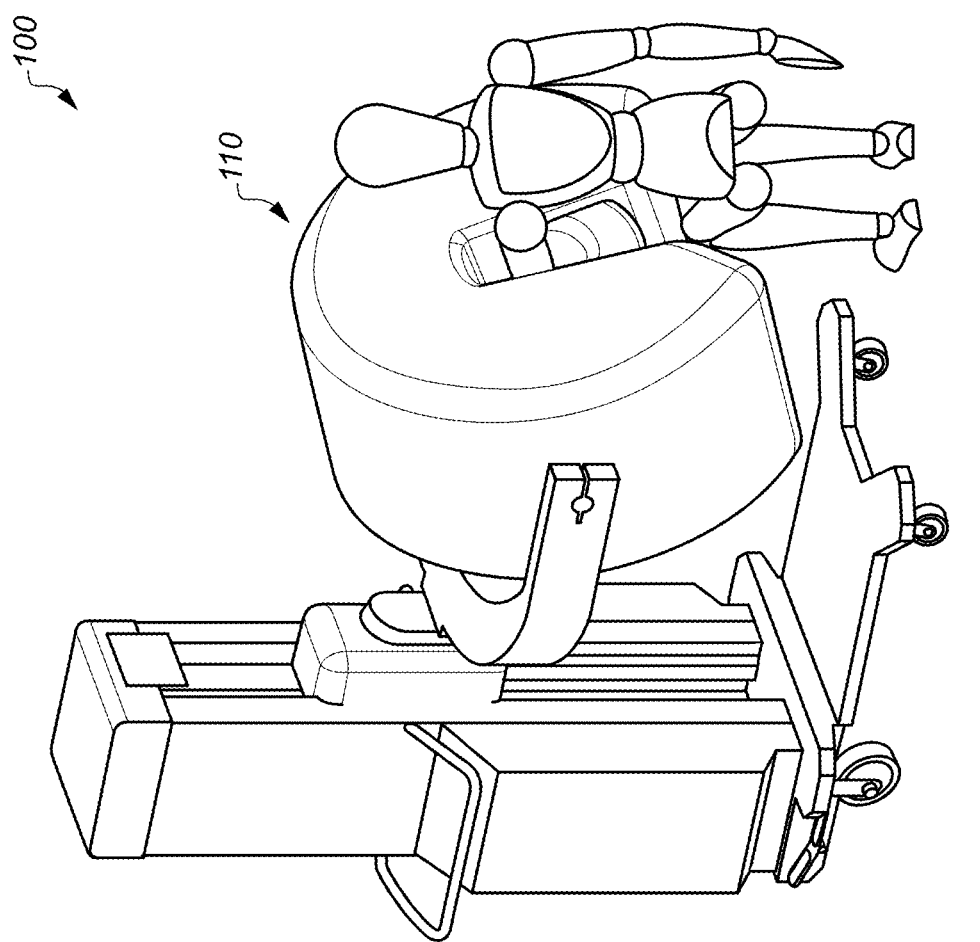
FIG. 4 shows a configuration of the extremity imaging system for volume imaging of upper limbs.
Figure 5:
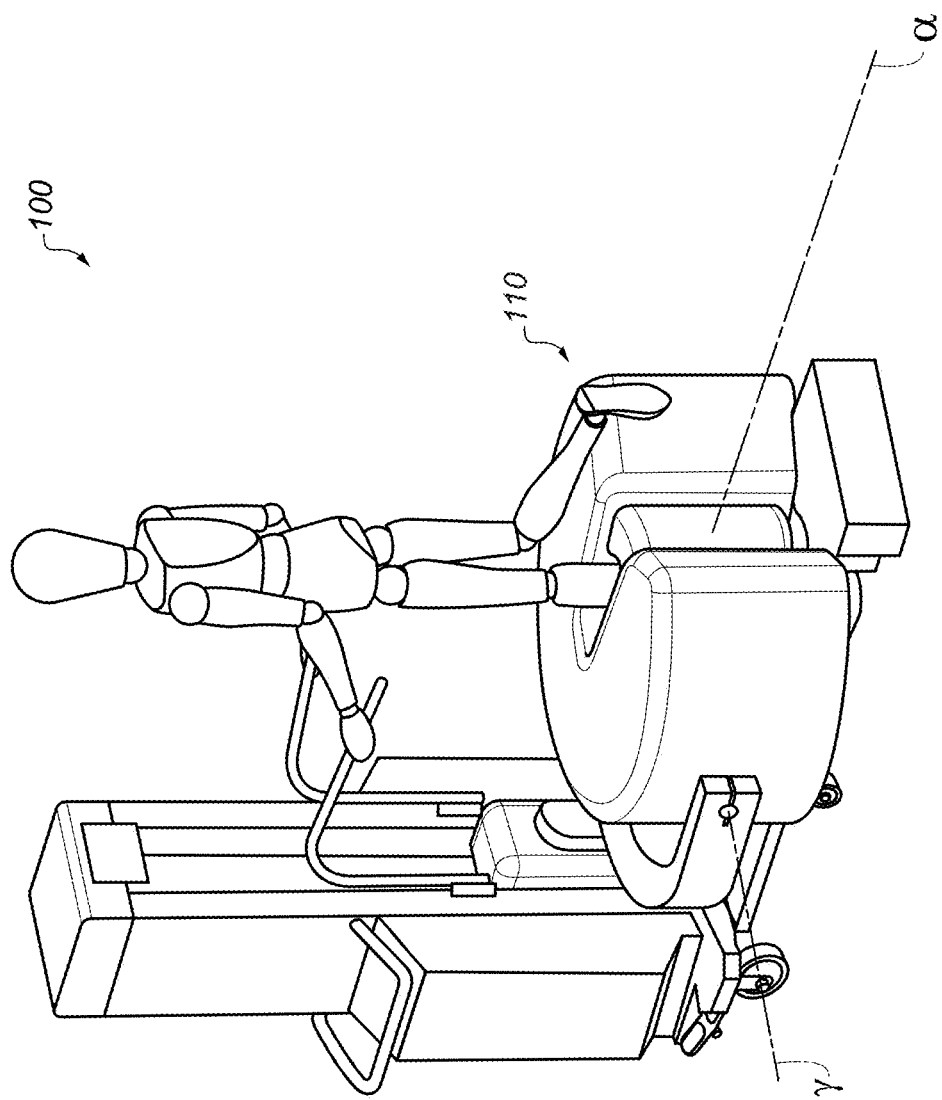
FIG. 5 shows a configuration of the extremity imaging system for volume imaging of lower limbs.

FIGS. 3 through 5 show the use of CBCT imaging apparatus 100 for acquiring volume image content from different extremities. FIG. 4 shows a configuration that can be used for imaging of upper limbs such as, arms, hands, wrists, and shoulders. FIG. 5 shows a configuration of imaging apparatus 100 that can be used for imaging of the lower limbs, such as legs, knees, and ankles, for example. A variety of patient positions are possible, including sitting, standing, and weight-bearing.

A preferred system for embodiments described herein is a cone beam computed tomography (CBCT) system with an integrated Automatic Exposure Control (AEC) function based on body part and size of the anatomy. The system allows for adjustment of a range of available techniques (kVp, tube current, exposure time). The system further allows for the characterization of noise index as a function of body part size over the available technique range, as well as minimum/maximum allowable dose/technique. The AEC function in CT and CBCT imaging is preferably implemented by capturing one or more scout images and deducing relevant parameters, such as patient size and material density. In some cases, AEC measurement is obtained from the detector 24 itself, without use of a separate, dedicated AEC sensing device, although such a device could also be used to implement the AEC function.

Selection of a preferred noise level relates to patient dose. In some cases, the noise level is presented as a number, for example as the ratio of the noise and the mean of the linear attenuation coefficient, or simply noise in Hounsfield units (HU) for a known phantom of standard size. For a modality such as CBCT extremity imaging, however, users may not know how these numbers relate to the imaging function and to the ability to perform diagnostic tasks.

In conventional CT imaging, computation of the exposure to be used in patient imaging is typically performed using results from systematic scanning of one or more phantoms under highly controlled test and calibration conditions. Phantoms are typically cylinders of different sizes, formed of PMMA or other suitable material, including beads or inserts of various densities. Scanning is performed under a range of operating conditions, such as peak tube voltage (kVp), tube current (mA), and exposure time (ms). 3-D reconstruction is performed and a noise factor obtained quantifying the noise in the reconstructed volume as described previously. Noise factor is typically quantified according to a ratio of noise to actual signal content. Embodiments of the current disclosure employ noise factor setting as a metric for use in setting AEC levels. Analogous with operation of a camera, the noise factor measurements that are used effectively provide a shutter setting in cooperation with the AEC. The AEC "shutter" controls the amount of radiation that is directed toward the imaged subject, based on some measurement of the radiation energy.

Accordingly to a method of the present disclosure, the AEC function is set up based on variable noise factors, anatomy size, and technique selection (such as kVp). The AEC capability can then be used to indicate a suitable exposure time product (mAs) for the patient. Optionally, one or two low dose scout images of the subject can be used to estimate anatomy size for using the generated noise data. Similar approaches can be implemented for CBCT imaging.

In order to offer an index that is related to noise level and dose for acquiring CBCT image content of particular anatomy, an embodiment of the present disclosure provides a graphical display showing volume image content, from a comparable subject or phantom, that is representative of a selected noise level. The operator can then select an exposure setting based on an acceptable noise level as shown on displayed images.

Figure 6A:
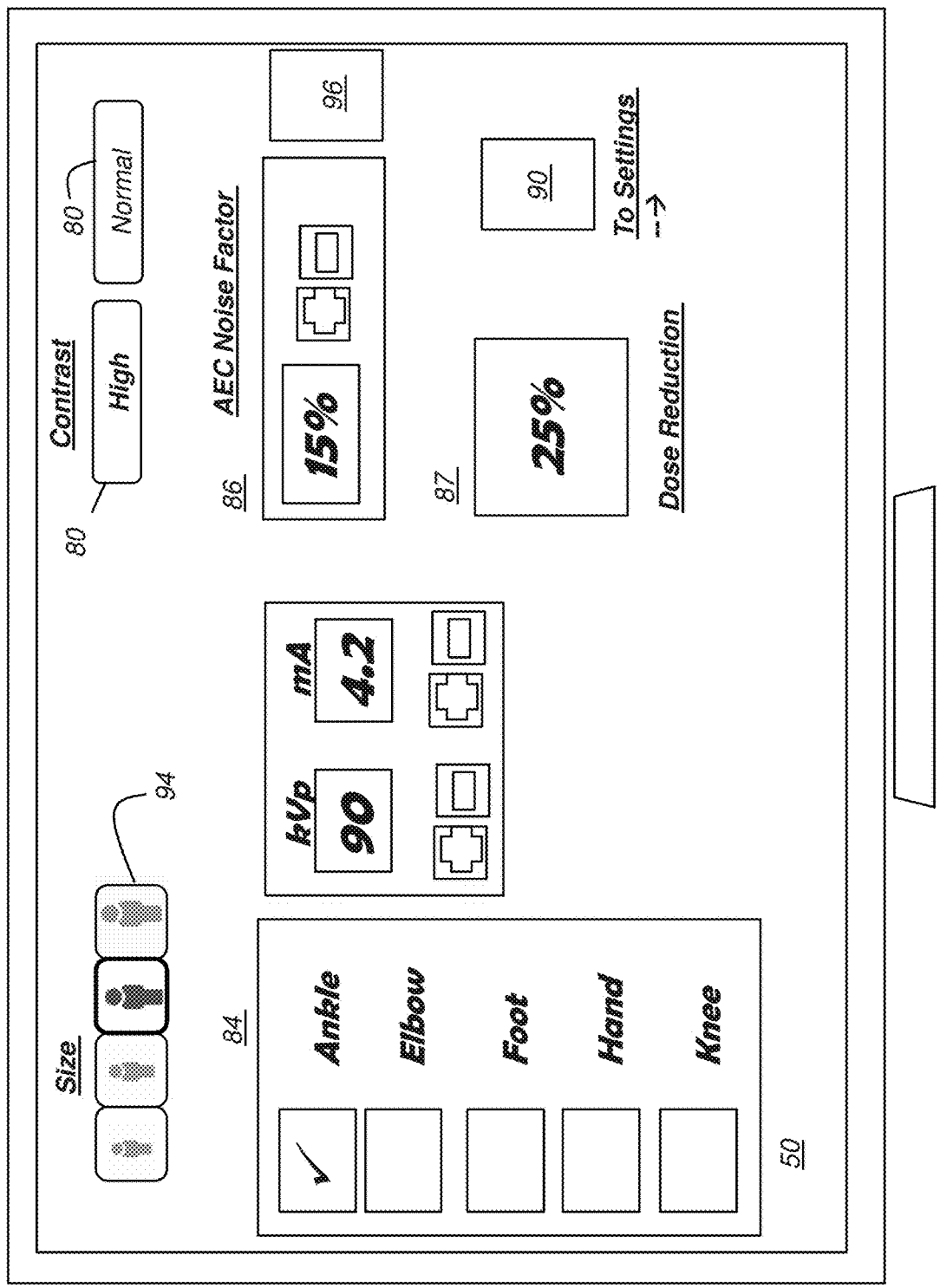
FIGS. 6A, 6B, and 6C show plan views with layout arrangements for an operator interface that can be used for a CBCT or other volume imaging apparatus.
Figure 6B:
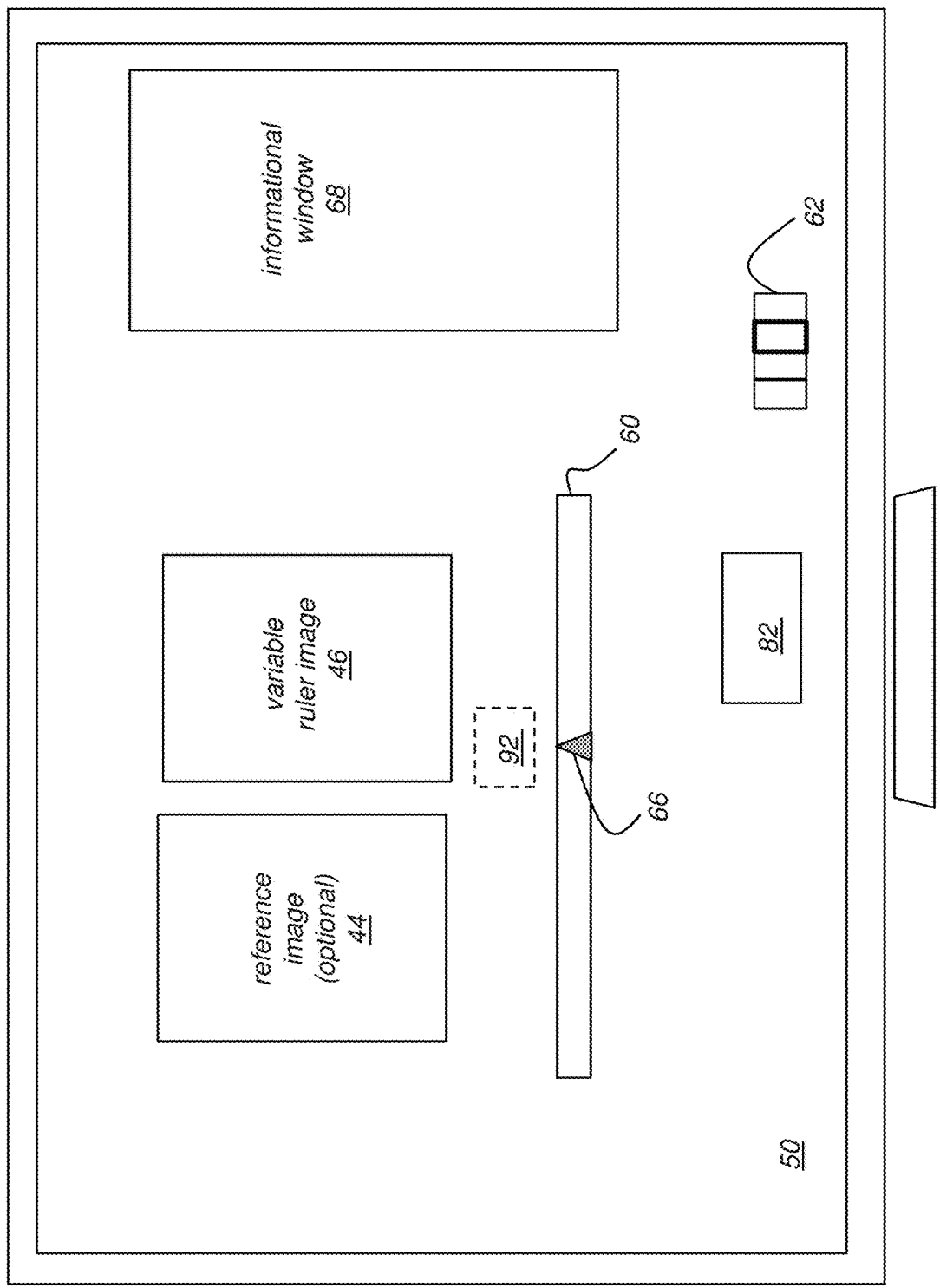
Figure 6C:
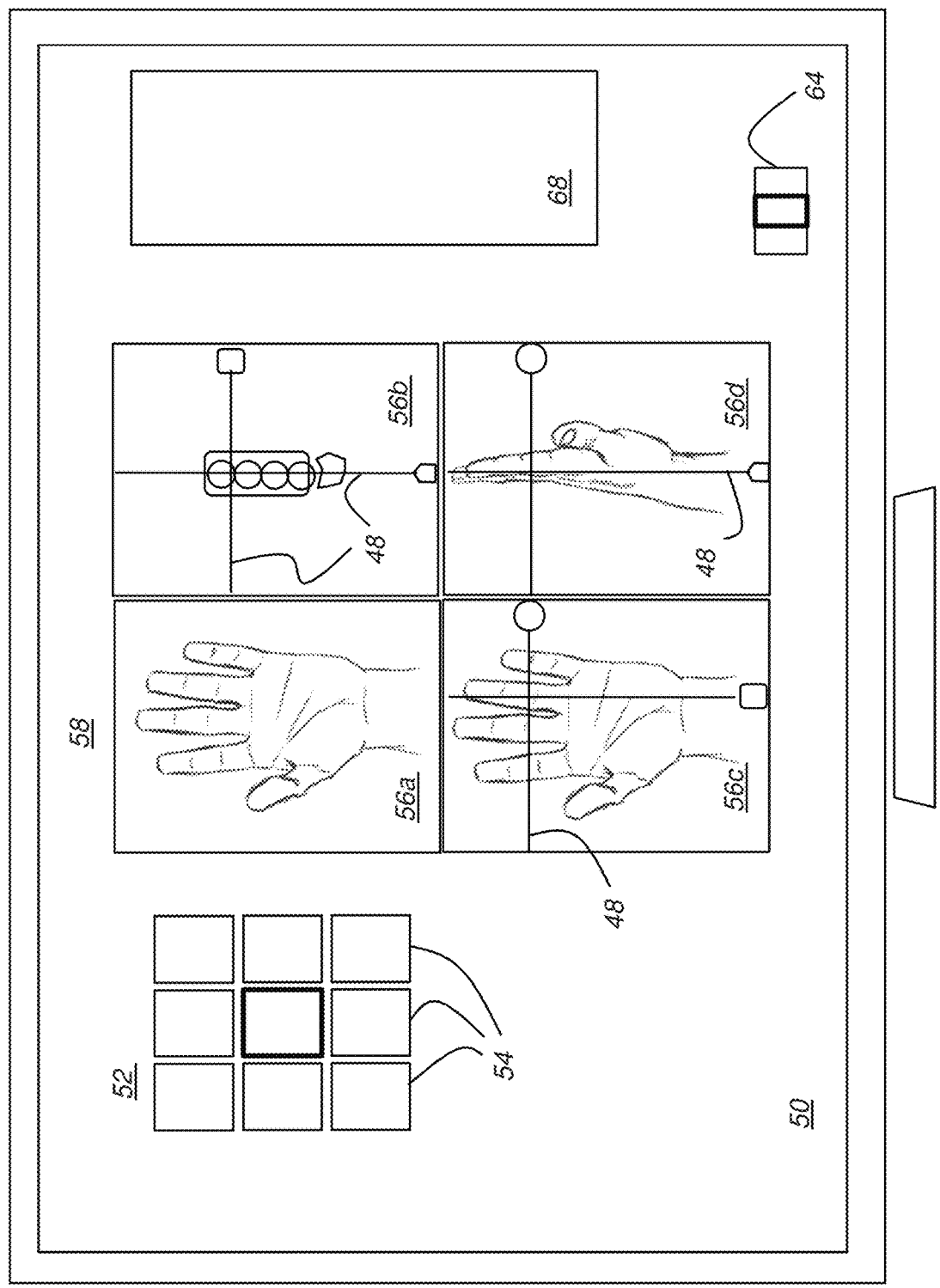

The schematic diagrams of FIGS. 6A, 6B, and 6C show an exemplary user interface display 50 that allows system users to perform noise level selection based on visualization of the desired diagnostic image quality.

Each noise level corresponds to a known technique in terms of kVp and mAs for acquiring the 2-D projection images that will be used in 3-D reconstruction for a type of anatomy according to an embodiment of the present disclosure. Advantageously, the user who configures noise level for the volume imaging apparatus can make an selection/decision by viewing data that has been rendered from the reconstructed volume, such as volume image data obtained from image acquisition and reconstruction using a standard anthropomorphic phantom.

FIG. 6A shows an user interface display 50 of an entry screen for specification of anatomy type, size, and technique factors. In a technique setup area 84, the operator specifies anatomy and relative patient size for storing of the subsequent parameters. A set of size selector buttons 94 can be used, indicative of a weight/size range. Alternatively, a specific weight value can be entered. Default technique values for kVp and mA are entered for the specified anatomy and size. Alternatively, specific kVp and mA values can be entered.

An AEC noise factor is entered. In a noise factor entry window 86, a numeric value or other type of value indicative of the acceptable noise factor for the AEC can be entered. Alternatively, the system can provide a default value.

Optionally, the user may select visual setup of the noise factor using control 96 to disable the manual entry noise factor entry window 86 and invoke one of the embodiments of the disclosure for visual selection of the noise factor. Entered values, including visually selected values, can be stored to provide technique setup parameters for day-to-day operation of the CBCT system.

A dose reduction value 87 can be displayed on the display.

An optional contrast selection 80 allows entry of separate specifications for high or normal contrast exams.

A control button 90 can be provided to display additional settings or to move to another settings screen of FIG. 6B.

Dose reduction value 87 displays dose reduction for the sized body part based on the noise factor selection. Preferably, dose reduction value 87 cannot be manipulated by the operator.

The interface of user interface display 50 shown in FIG. 6A can be made available to set up each body part, e.g. knee, hand, and the like, with individual screens for different sizes (e.g., adult and child), different types of exams (e.g., high contrast bone exams and low-contrast soft-tissue exams), or even different practitioners.

Referring to FIG. 6B, there is shown an arrangement of display elements and tools that can be used for noise level selection in various embodiments described with reference to subsequent FIGS. 7A, 7B, and 7C.

Using a model display of FIG. 6B, each user interface display 50 for noise level selection preferably provides a variable ruler image 46 that can be rendered using different noise factors and an optional reference image 44 that can be used as a guide for adjustment according to noise factor. A slider bar 60 with indicator 66, or similar operator interface utility, also referred to as slider or ruler control, allows the operator to simulate adjustment of the noise factor, and correspondingly, the dose level, while viewing variable ruler image 46 and the optional reference image 44. An optional dose penalty value 92 can be displayed, such as corresponding to the setting of indicator 66 on the slider bar 60. The dose penalty value 92 can be expressed in percentage or in milligrays, or some other value meaningful to the operator/practitioner. Element 62 is a control/selection button.

An image quality ruler can offer a selection of images assembled in order of increasing or decreasing quality of a variable image quality attribute, such as sharpness or noise. Each ruler image includes an associated image quality value, for example, a noise index. The user can select the desired rendering using control button 62 for the noise level corresponding to one of the ruler images selected on a sliding scale. An arrow or indicator 66 is movable to highlight and select a desired noise level. The corresponding image can be highlighted, such as outlined or enlarged, for example, in contrast to other images. The slider bar 60 is preferably set up such that the left-most position of the indicator 66 within slider bar 60 corresponds to the highest noise factor available for the selected anatomy and the rightmost position of the indicator 66 corresponds to the lowest noise factor available for the selected anatomy. Other setups can be employed. For example, a reverse setup with the highest noise factor on the right and the lowest of the left.

The corresponding selected noise level 82 for a selected rendering can be provided as an input to the automatic exposure control of the system (AEC). An informational window 68 of FIG. 6B shows selected values, has additional operator controls, and/or provides other information related to the particular exam, such as exposure conditions, dose and/or size of the anatomy. Numeric noise ratios for the displayed and selected noise levels can also be displayed.

The display interface 50 comprising the image quality ruler as shown in FIG. 6B can be available for display and manipulation as needed by the operator who configures the system defaults for patient imaging. Interface display 50 of the ruler can be provided on the main control screen of FIGS. 6A, 6B, or in a separate window or control screen, invoked upon entry of a command instruction, for example. Images for comparison can be displayed in a number of ways, including vertically, horizontally, or with a tabbed arrangement. Various ways of comparing images for noise level are described subsequently. According to an alternate embodiment, the operator can be presented with a single image and a control knob or other on-screen command or instruction feature for modifying the displayed image to show a suitable noise level.

FIG. 6C shows an exemplary user interface display 50 that allows the operator to select a specific location and view of a reconstructed 3-D volume. Screen selections can be made using a selector (such as a mouse, key stroke, pointer, or other input) or a touchscreen for accepting operator instructions.

Interface display 50 illustrated in FIG. 6C includes a case selection block 52 that displays one or more views 54 (such as thumbnail views) of stored volume data that is available for operator selection. This can include patient images and/or a library of images from scanned phantoms or from cadavers, where the images have been generated at different exposures to support noise level selection for different diagnostic tasks.

A view display area 58 shows one or more views of volumes selected from case selection block 52 to allow an operator selection of a specific point within the volume. In the embodiment shown in FIG. 6C, a block 56a shows a reconstructed 3-D view of the complete phantom or other subject. A block 56b shows an axial slice view of the 3-D reconstruction, with selection lines 48 that show the relative positions of sagittal and coronal sections. A block 56c shows a coronal slice view of the reconstruction corresponding to one of selection lines 48. A block 56d shows a sagittal slice view corresponding to the other selection line 48. By manipulating the position of selection line 48, the operator can obtain various sagittal and coronal slice views of the reconstruction, showing the image appearance for the corresponding case.

Figure 1A:
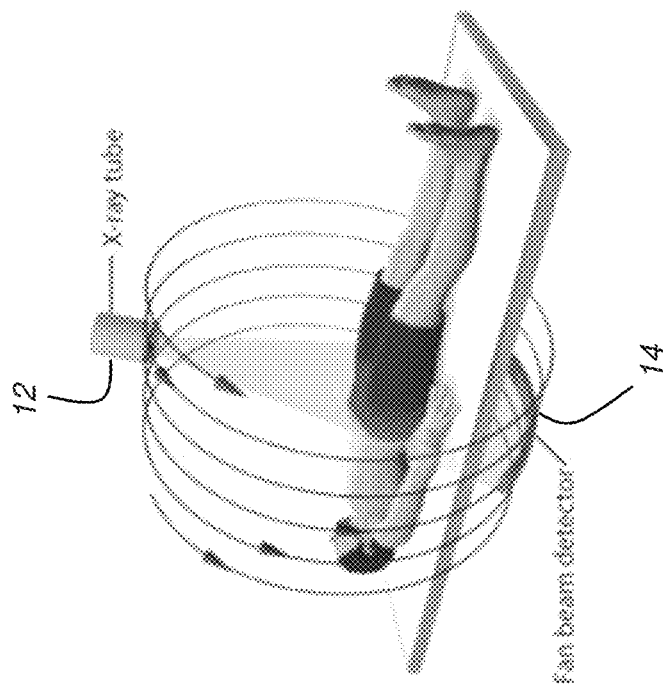
FIG. 1A is a schematic view showing a computed tomography apparatus.

The coronal and sagittal views 56c and 56d shown in FIG. 6C have additional selection lines 48 for identifying the desired z-position in the volume (FIG. 1). Once the desired x-, y- and z-coordinate position in the reconstructed volume has been selected using selection lines 48, the user selects/clicks on or otherwise selects the desired view (i.e. axial, sagittal, coronal, or 3-D) on display 50. Based on view selection, an image quality ruler for the same view is assembled/displayed from the stored multiple volumes of the same image content.

An optional control button 64 selection specifies the ruler or other interface utility type.

For AEC setup, the volumes that can be used for display rendering and view manipulation in FIG. 6C preferably differ in noise level due to differences in X-ray exposure level. It is noted that these stored multiple volumes preferably include appropriate metadata, i.e. additional ancillary data about the patient/phantom, such as size and noise level in the reconstruction, and data about the system. e.g., technique settings such as kVp and mAs selection. The ability to select different views, e.g., axial, sagittal, and coronal slices in different locations of the 3-D volume may be useful when comparing 3-D reconstructed volumes from different imaging systems, for example from MDCT and CBCT systems or from different CBCT systems.

Figure 7A:
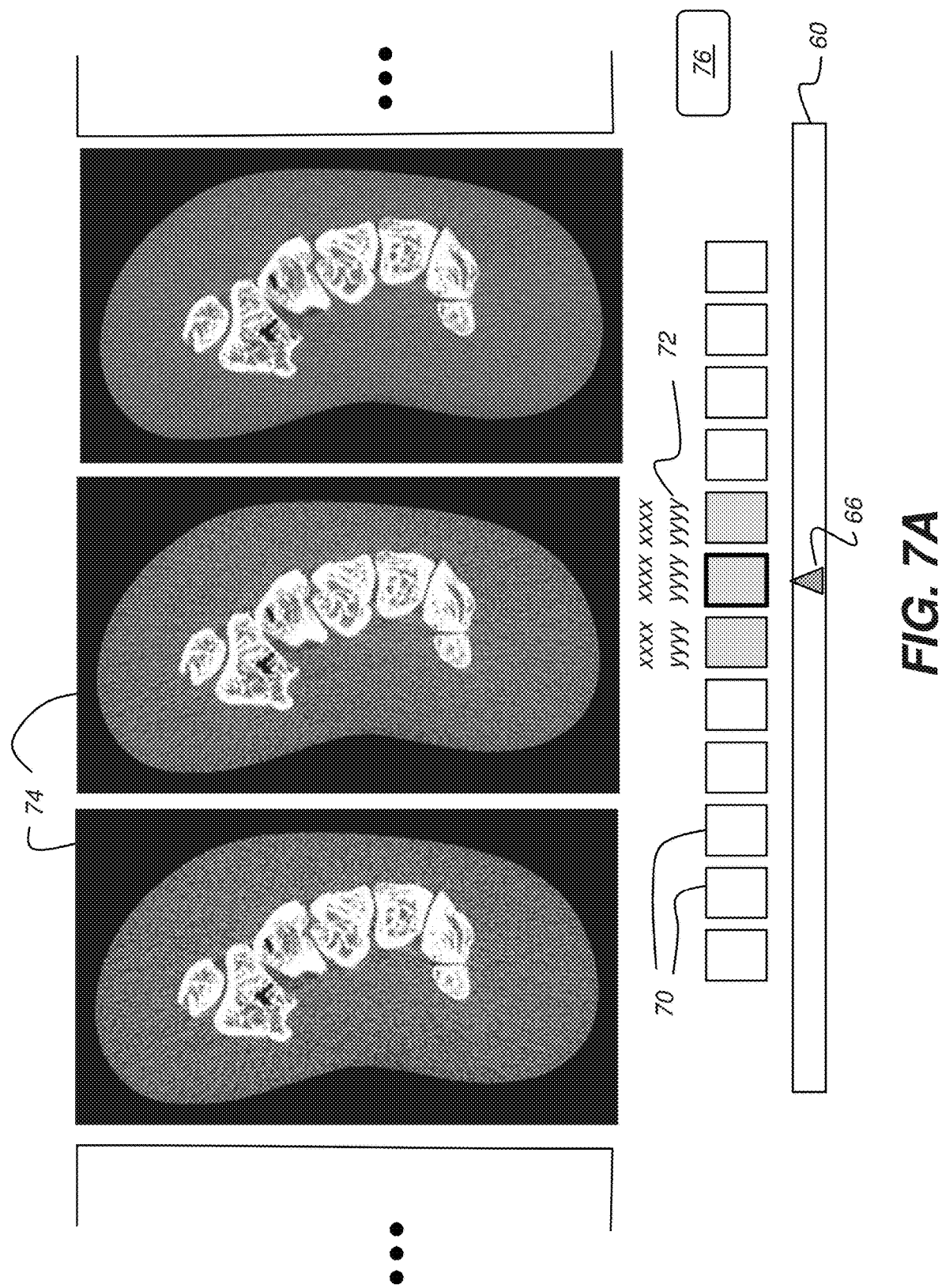
FIGS. 7A, 7B, and 7C show exemplary ruler selection arrangements displayed on the operator interface for specifying different noise levels.
Figure 7B:
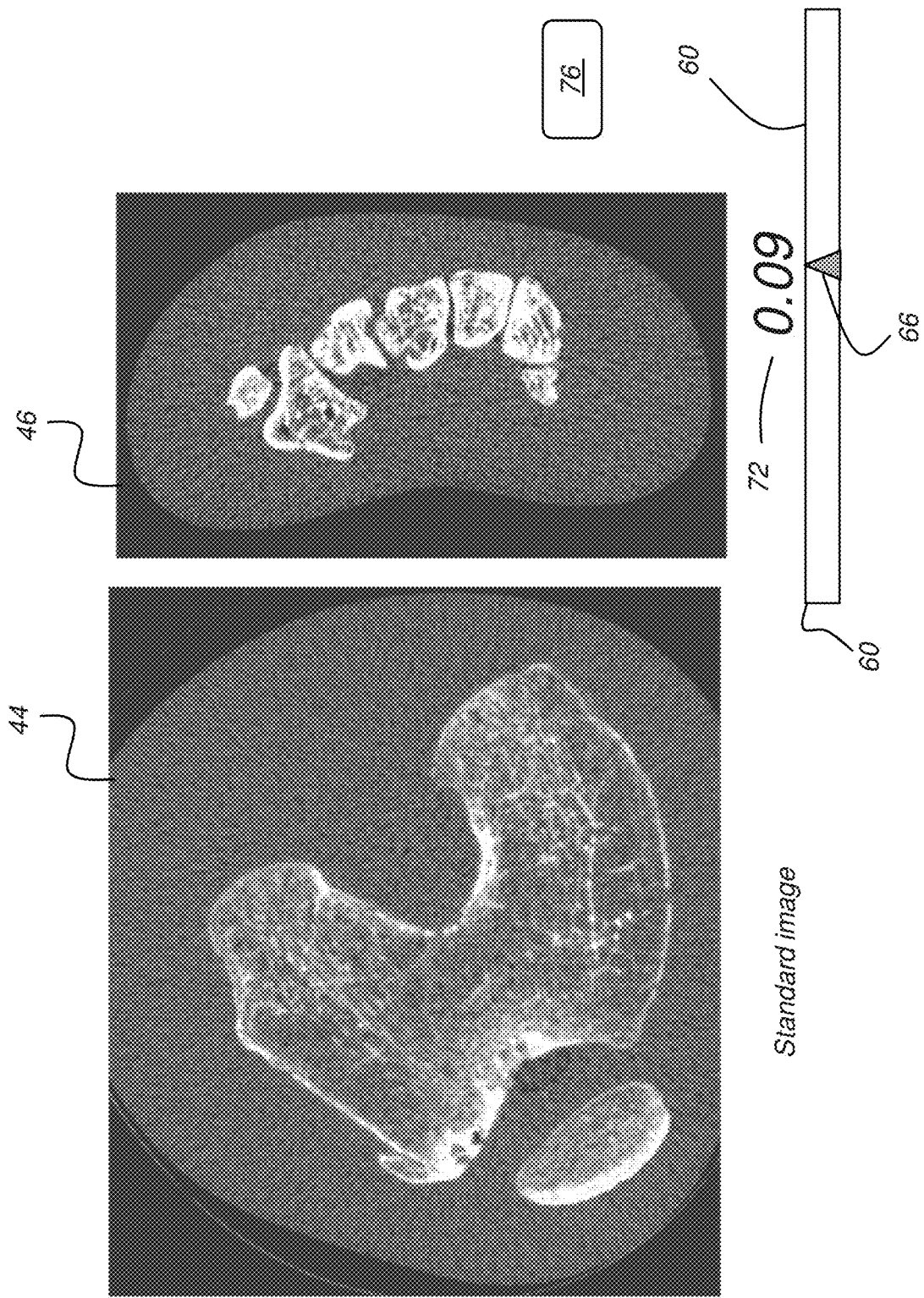
Figure 7C:
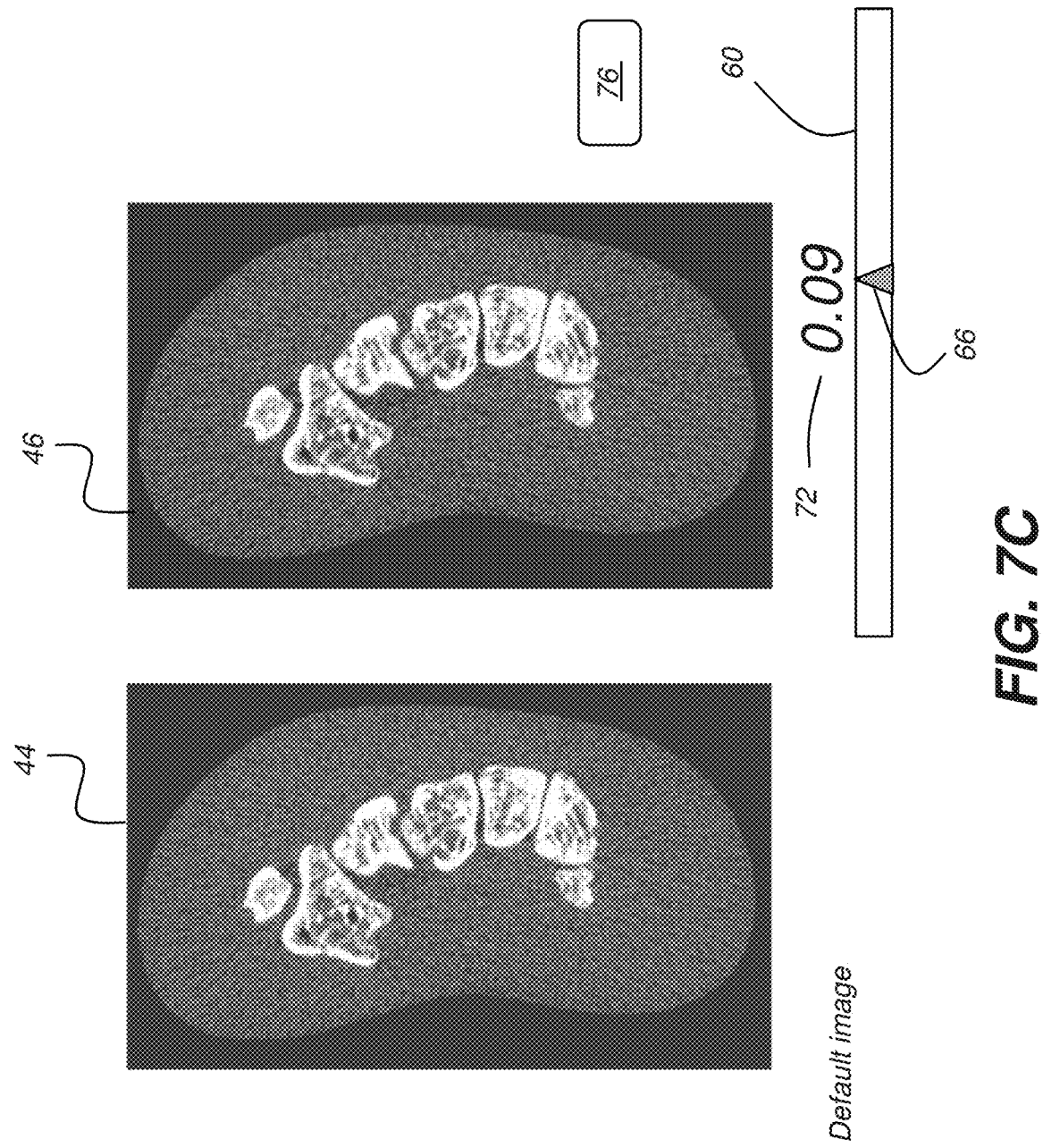

FIGS. 7A, 7B, and 7C show some of the different types of rulers and related utilities that can be presented for selection of noise level and corresponding exposure levels as part of CBCT apparatus setup.

Referring to FIG. 7A, a control screen (user interface display 50) presents the viewer with an ordered arrangement of images, with a predetermined number of images displayed, such as three images at a time as shown in FIG. 7A. The image ordering for a progression of images uses the same subject matter or content, and relates to noise level and corresponding exposure and, optionally, also to technique settings used to obtain the image. Viewing and selecting exposure results from the ordered progression of images allows the user to more clearly visualize the impact of a particular exposure level on diagnostic image quality, allowing reduced radiation to be received by the patient.

Still referring to FIG. 7A, ruler images 74 can reference/correspond a number of thumbnail views 70, wherein each thumbnail view 70 has a corresponding ruler image 74 with a distinct noise level. A ruler image 74 can be displayed, alongside an adjacent image or images 74, preferably at the next highest and next lowest increments of noise level. Exposure data 72 related to the displayed images can show a noise or exposure index and/or values related to image acquisition, such as kVp and mAs values, or patient dose, for example.

The viewer operates the control screen of FIG. 7A using slider bar 60 and indicator 66 to identify the image that corresponds to an acceptable noise level for the type of exam that corresponds to the configuration being done. When the configuring operator is satisfied with the currently selected noise level, a control button 76 or other operator instruction entry feature is used to select/identify/store the corresponding noise level/exposure setting.

The operator interface shown in the example of FIG. 7B uses a different approach (than that shown in FIG. 7A) for obtaining operator specification of noise level.

In FIG. 7B, side-by-side images are displayed/compared for relative noise level. The operator is presented with a reference image 44, that can be a fixed, sample image at a predetermined/suitable noise level for a particular series of exams. No adjustment with regard to noise level would be allowed/provided for this fixed image. The reference image 44 can be a standard image, or even an image showing other anatomy, but having a noise level that is considered acceptable for a particular exam type. The other image that displays, variable ruler image 46, corresponds to the anatomy to be imaged and can allow variable adjustment. Adjustment of the indicator 66 on slider bar 60 can provide a sliding scale as an interface for operator selection, allowing the operator to dynamically change the appearance of the variable ruler image 46. The noise levels that are shown correspond to the indicator 66 setting and can be discrete noise levels for variable ruler image 46 or can be adjustable over a range. The system can then set up the AEC according to the operator selection.

The arrangement shown in FIG. 7B allows the user to load a reference image, such as a DICOM (Digital Imaging and Communications in Medicine) image from a reference system that has the predetermined/desired noise level, and compare it with the variable ruler images. The method of the present disclosure can present both images with the same window/level and magnification. This may be desirable for users that either currently have MDCT systems or other CBCT systems.

It is preferable that reference images 46 displayed by the system conform to known standards, such as the DICOM standard, for example. The DICOM standard is the result of ongoing work of an independent, international organization of biomedical professionals with interest in medical imaging and related image acquisition and storage systems and practices. Manufacturers and developers of medical imaging products comply with the DICOM standards related to their particular disciplines.

As part of the DICOM architecture, images are stored in particular formats and have accompanying metadata that identifies various patient and medical information and describes how the images are to be used. Among image metadata for DICOM images are values indicative of photometric interpretation, specifying the intended interpretation for the image data. By way of example, useful photometric values can include data related to monochrome or color presentation, luminance and chrominance values for color pixels, and color transform data between various color standards used for display or printing.

In general, images conforming to the DICOM standard and displayed on a monitor that is calibrated to the GSDF (Grayscale Standard Display Function) are preferred for meaningful comparison of images from different systems. Images can be stored and managed using PACS (picture archiving and communication system), which works compatibly with the DICOM data. PACS includes tools for network transfer, presentation, storage, and retrieval of medical images. The PACS standard helps to improve delivery and use of medical images between systems.

The operator interface in the example of FIG. 7C shows system default AEC setup for particular anatomy as reference image 44. Adjustment to variable ruler image 46 is again provided using slider bar 60 and indicator 66. This side-by-side arrangement allows the user to enter settings data using a particular view of the imaged anatomy. Default treatment for the desired view gives the configuring viewer a starting point for customizing the noise factor and the corresponding exposure. As also illustrated in FIGS. 7A and 7B, exposure data 72 can be displayed. When the configuring operator is satisfied, control button 76 is used to select/identify/store the corresponding noise level/exposure setting.

Once the noise level is selected, the display can also provide the option to show the full, reconstructed volume at that noise level for evaluation.

It can be appreciated that the methods described and shown are useful for visualization of noise level selection over conventional methods that use numerical entry or selection.

Applicants submit that the selection of the preferred noise level using the disclosed visualization provides advantages (such as being intuitive to the user), based on exemplary images, as compared with using noise ratios that are simply displayed as numerical values below the images.

Calibration of the AEC

Methods for AEC calibration are known in the field of CT imaging. One such calibration method uses cylindrical phantoms of different sizes that span the corresponding range of sizes expected from the anatomy. Phantoms made from PMMA or phantoms filled with water are common.

In the calibration procedure, phantoms are imaged using the standard scan protocols, for example, in terms of filtration, kVp, tube current, exposure time, number of projections and angular resolution in CBCT, number of slices and scan speed in CT. Multiple scans are acquired at different combinations of kVp, tube current, and exposure interval.

The acquired scans are then reconstructed using the standard reconstruction protocols available on the system. Finally the reconstructions are analyzed in terms of noise.

Common metrics for noise are HU or the noise of the linear attenuation coefficient of the material (PMMA, water), or the ratio of the noise and the mean of the linear attenuation coefficient. Using this methodology, the noise in the reconstructions, e.g., the noise factor, can be characterized as a function of technique. e.g., kVp and tube current, and size of the anatomy. As described in US Patent Application Publication No. 2015/0359501 entitled "Systems and Methods of Automated Dose Control in X-Ray Imaging" by Eronen et al., one function of the AEC is to estimate size of the object imaged, typically from one or two scout images acquired at low exposure. This size estimation can be performed by an algorithm or using a physical sensor that senses the intensity of X-rays transmitted by the object. Then the AEC calibration data and the input from the user regarding the desired noise level can be used to generate the appropriate technique for CT or CBCT acquisition.

Ruler Image Generation

It can be appreciated that different views of volume data are needed, based on the anatomy and diagnostic task for which the noise level is being identified. The variable ruler images that display for operator guidance can be generated using various methods, for example:

(1) image captures of phantoms or cadavers at different exposure levels followed by image reconstruction as implemented on the system;

(2) image captures of phantoms or cadavers at different exposure levels followed by image reconstruction as implemented on the system including disease features added by image simulation;

(3) a single capture of actual anatomy with a disease feature at the lowest noise level that can be achieved on the system, with a progression that shows added noise corresponding to known lower exposure levels using image simulation.

Reference is hereby made to U.S. Pat. No. 7,480,365 entitled "DOSE REDUCED MEDICAL IMAGE SIMULATIONS" (Toepfer), incorporated herein in its entirety by reference, regarding the use of image simulation techniques to add noise to 2-D higher dose projections. The presence of disease features in the ruler images, such as fractures or low contrast tumors, is particularly advantageous to support task-based optimization of image quality at the lowest possible dose.

According to an embodiment of the present disclosure, image quality rulers have perceptually equidistant steps (single or multiple just-noticeable differences, JNDs) in the depicted image quality attributes. This may be difficult to accomplish using the available exposure settings on the system. In addition, a perceptually calibrated scale for the image quality attribute, in this case noise, may not be available. In such cases, any assembly of images in ascending or descending order of the image quality attribute with readily perceived quality differences between adjacent images, can be suitable to perform the selection of noise level.

Ruler image generation for AEC setup can be performed using the AEC calibration tables and the AEC algorithm or sensor for size estimation. i.e., a few low dose scout images are taken for any of the three ruler image generation methods/sources [(1) thru (3) described above] of variable ruler images described above and the PMMA equivalent size is estimated. Using the relationship between technique, size and noise factor established in the AEC calibration, the appropriate technique setting (for example in terms of kVp and tube current in mA) for each of the ruler images can be calculated.

For the first two ruler image generation methods/sources [(1) and (2) described above], a scan with the appropriate technique to achieve the desired noise factor would be performed. For example, if a ruler has seven different noise levels, seven repeat scans of the phantom or cadaver at different techniques would be performed followed by 3-D reconstruction and storage of the resulting volume for future use in a interpretable format, e.g. DICOM format.

For the third ruler image generation method/source [(3) described above], a single higher dose scan would be performed representing the lowest possible noise level and other higher noise ruler levels would be generated by image simulation. As before, the final reconstructed volumes can be displayed, stored, or transmitted for future use. In ruler image generation method/source (3), it is also possible to run the reconstruction on the high exposure with the lowest noise only. Then a mathematical model of the reconstruction process can be used to add additional noise to the selected reconstructed slice according to the noise factor selected by the user using indicator 66 on slider bar 60. This method of adding noise would generate a continuous scale of simulated noise factors, as opposed to the discrete scale of noise factors used with the other methods described.

The lowest and highest noise levels presented on the ruler are preferably determined/driven by practical constraints, for example:

(1) the tube output and the available range of X-ray techniques on the system (such as tube current, exposure time and kVp), (2) specified predetermined upper and lower dose limits to guarantee the desired diagnostic quality and limit the dose to the patient.

Figure 8:
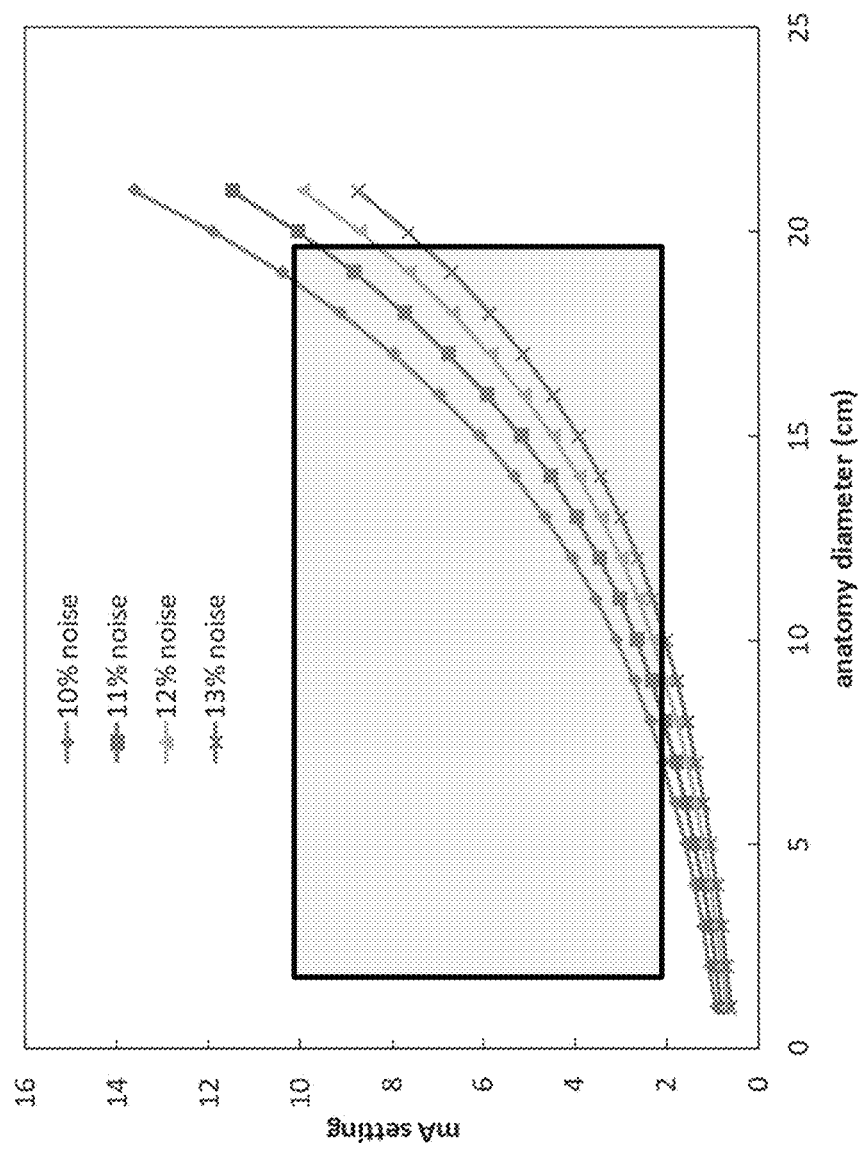
FIG. 8 is a graph that shows typical bounding conditions for the mA setting based on body part diameter.

Referring to practical constraint (1) above, the graph of FIG. 8 shows the required mA to achieve a series of noise factors as a function of effective body part diameter on a CBCT extremity imaging system such as the one shown in FIGS. 3 and 4. The values apply to a fixed kVp setting within the kVp range that the system can generate. The lower and upper mA limits of the system are 2 and 10 mA respectively. This curve set was obtained from a calibration of the AEC using PMMA phantoms of various sizes. Using the calibration data in a different way, for example for a typical knee of 12.5 cm PMMA equivalent diameter, the system can produce noise factors between 0.16 at the lower 2 mA and 0.06 at the upper limit of 10 mA. Within these constraints the lowest quality ruler image for this case can be defined with a noise factor of 0.16, for example. This setting corresponds to the leftmost position of indicator 66 on slider bar 60 in FIGS. 6B, 7A, 7B and 7C. Correspondingly, the highest quality ruler image has a noise factor of 0.06, equivalent to the rightmost position of the indicator 66 on slider bar 60.

In addition, the system can support two or more different noise levels for AEC setup. In extremity imaging, for example, a higher noise level can be more suitable for bone exams, such as fractures, which have high image contrast and therefore require lower noise resolution of the system and lower exposure. Soft tissue exams, on the other hand, requiring visualization of ligaments or muscle, typically have low contrast and require improved contrast resolution, a lower noise index, and higher exposure.

According to an alternate embodiment, ruler images and software can be distributed for viewing on a non-transient storage medium, e.g. DVD, flash memory or a hard drive on the system. Selections made using this system can be linked directly to AEC setup software or can be used for manual entry of numeric values to the AEC setup utility. This method also allows the user/service personnel to load DICOM images from other systems with preferred noise level, such as in the library of stored reference images.

In general, the manufacturer of CBCT apparatus provides a default set of noise factors to set up the AEC for different anatomy to be imaged. The operator interface described herein can be used to help customize the noise factor used for a particular site or application. This function can be performed globally, such as by adjusting the noise factor so that dose is reduced from the system default by a certain percentage. Adjustment to the noise factor can be customized by anatomy type or by practitioner preferences or site requirements. Use of the user interface ruler can help to obtain suitable customization.

The operator interface described herein and shown by reference to FIGS. 6A-6C can be a standalone application or can be integrated as part of the scan capture console. It may be advantageous to cache images in memory to reduce recall and display time.

Workflow for Using a Visual Tool for AEC Setup

Applicant's application/method employs a visual tool in the form of a ruler or other on-screen adjustment setting to select the desired noise level for a slice from a reconstructed 3-D volume. This noise level setting can then be stored as part of system configuration to set up the AEC. Thus, system setup and configuration as outlined in the present disclosure allows subsequent patient imaging to execute without operator consideration for noise level, exposure settings, or other variables.

First Workflow Embodiment

Figure 9:
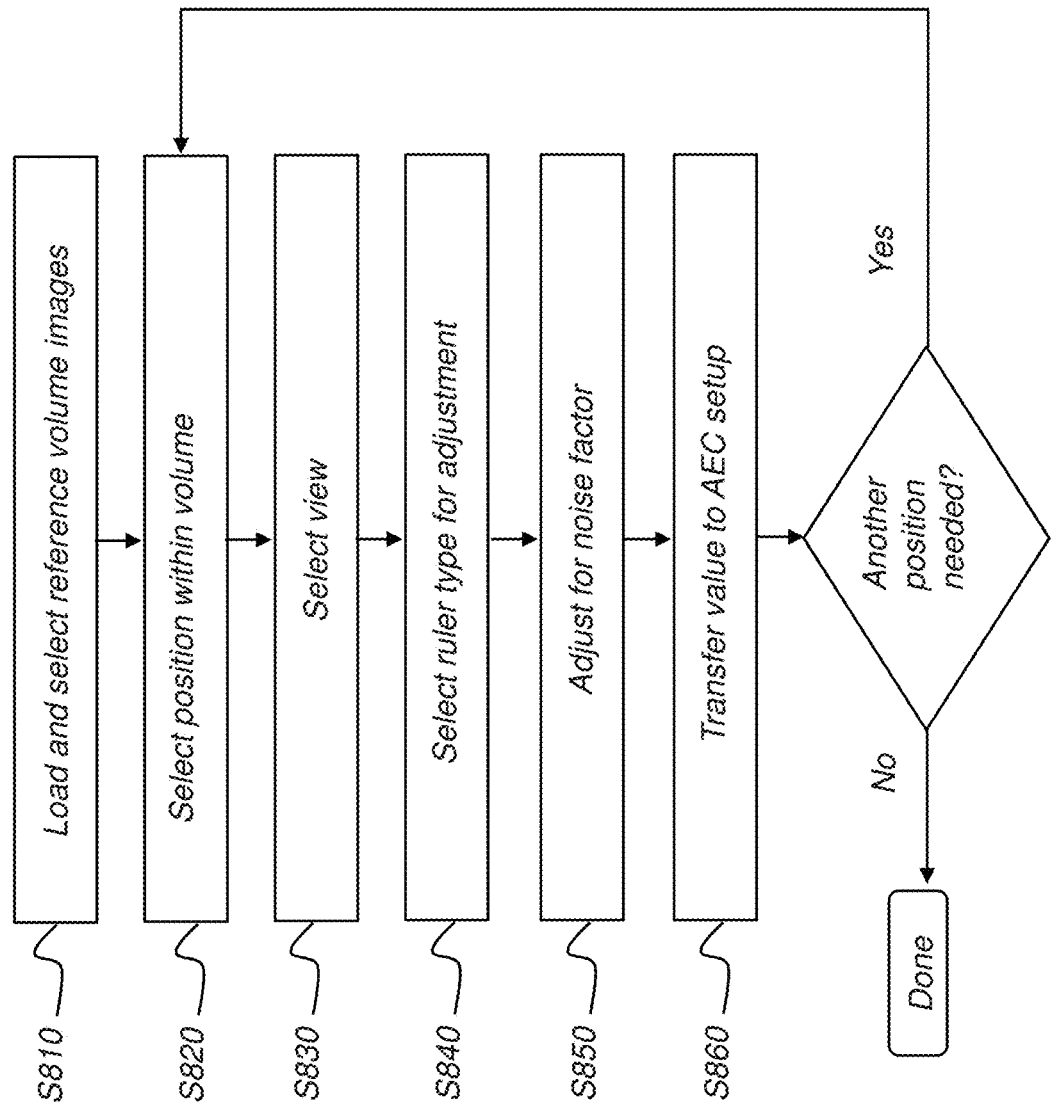
FIG. 9 is a workflow diagram for a system having an AEC setup utility that loads reference volume image data from an external memory or other source.

According to a first embodiment using the workflow sequence shown in the workflow diagram of FIG. 9, ruler images and the viewing software are supplied (for example, on a storage medium, e.g. DVD, flash memory or a hard drive on the system) and the software supports AEC setup of a CBCT extremity system. The user accesses the main screen of the software application. The software shows a list of available image sets, e.g., hand, hand with fracture, knee, knee with meniscus injury, and the like.

The user selects and loads the desired image volume set in a loading step S810. The image set is displayed in an arrangement suitable for viewing 3-D data sets, such as the one shown in FIG. 6C.

In a position selection step S820, the user selects the desired spatial position within the volume using selection lines 48 as positioning aids.

In a view selection step S830, the user indicates which view is desired for the ruler, i.e., axial, sagittal, coronal, or 3-D.

In a ruler selection step S840, using a menu on the GUI (such as control button 64 in FIG. 6C), the user selects one of the configurations of the ruler, such as shown in FIGS. 7A-7C. For example, the user can select the configuration shown in FIG. 7C. As a result, a new window opens displaying a reference image on the left side of the screen and, on the right, ruler images with a slider bar and pertinent information, e.g., noise factor, technique, and the like. The reference image may correspond to a noise index setting that is recommended by the manufacturer. The user may also exchange/swap the sides for the ruler-adjustable and reference images using an additional button on the GUI, or otherwise change the position of ruler and reference images on the display screen so that small differences in the display, ambient lighting, or the viewing angle do not affect the results.

In an adjustment step S850, the user manipulates indicator 66 on slider bar 60 (or other ruler mechanism) until the ruler image shows the desired result in terms of noise factor. On-screen instructions may emphasize that the decision should be made based on the ability to diagnose disease features, which is not necessarily equivalent with the lowest noise image.

A selection is then made. Once the selection is made, the GUI displays a numerical value associated with the selected ruler image, e.g., the noise factor metric or the relative change in noise in percent relative to the reference image.

In a transfer value step S860, the user can manually enter this value for the evaluated anatomy on the AEC setup screen, separately provided for the image capture software, as shown in the example of FIG. 6A.

After accepting the selected value, the user has the option to select another 3-D location and/or view of the same anatomy, to select a different data set on the main screen, or to exit the visual tool. If another selection is made, steps S820 though S860 would be repeated.

Second Workflow Embodiment

Figure 10:
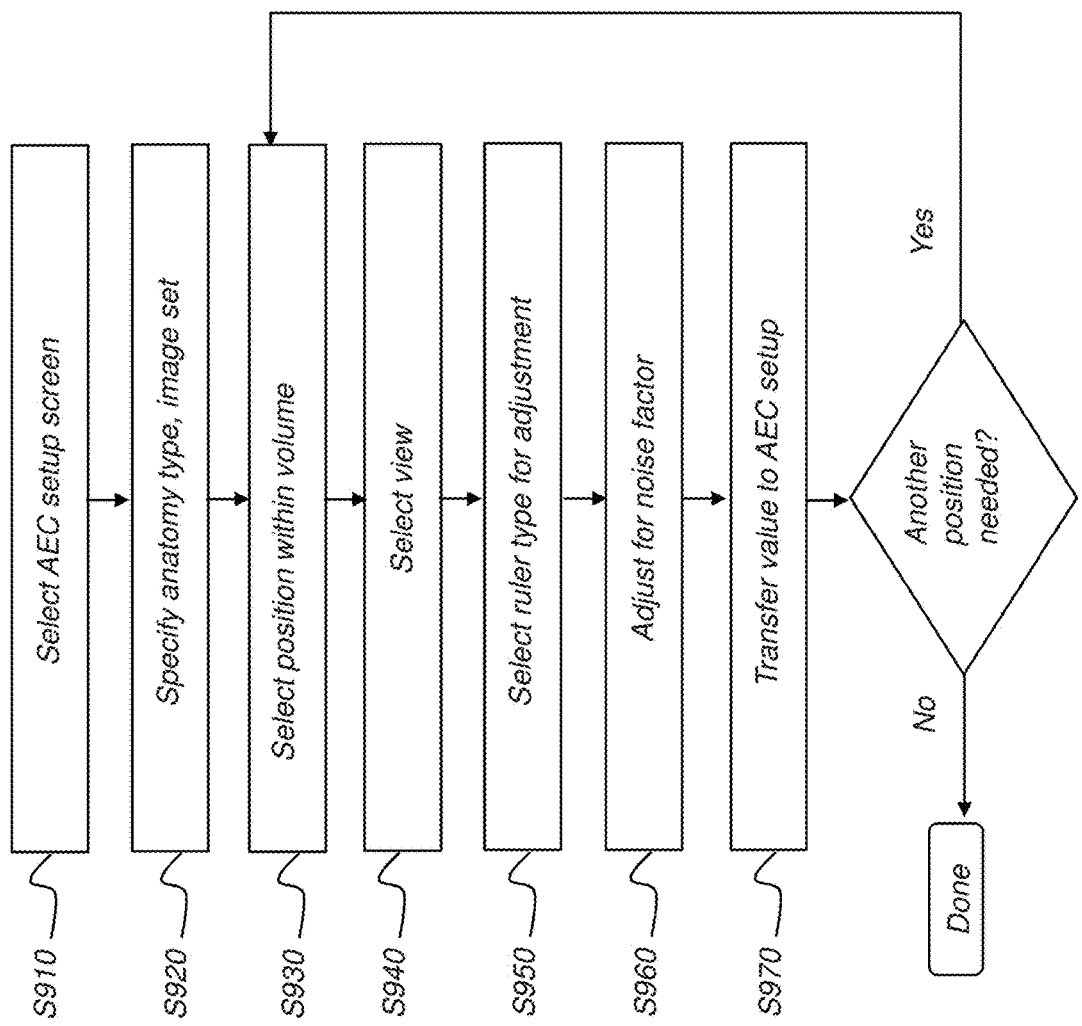
FIG. 10 is a workflow diagram for a system having an integrated AEC setup utility.

According to a second embodiment, the ruler images and the viewing software are part of the image capture software which optionally includes all 3-D image reconstruction, additional image processing, image display and communication with a PACS (Picture Archiving and Communication System) as a standard means to store and archive medical images. Steps for this workflow sequence are shown in FIG. 10.

In a AEC setup selection step S910, the user makes a selection (such as by pressing a button, such as selector button 94 in FIG. 6A) or otherwise enters an instruction on the GUI that selects visual AEC setup and displays a screen for AEC setup that is a part of the imaging system software. The selected AEC setup may be specific for individual anatomy, e.g., hand, humerus, femur, knee, or the like, identified by the user in a specify anatomy step S920, for example using the anatomy setup area 84 in FIG. 6A. Upon entering the setup utility, the viewer can also be presented with another selection menu that lists available image sets for the anatomy selected. e.g., hand, hand with fracture.

The image set is displayed in a new window in an arrangement suitable for viewing 3-D data sets, such as the display shown schematically in FIG. 6C.

In a position selection step S930, the user selects the desired position in the volume using positioning aids, such as selection lines 48.

In a view selection step S940, the user indicates which view is desired for the ruler, i.e., axial, sagittal, coronal, or 3-D.

In a ruler selection step S950, using a menu on the GUI (such as control button 64 in FIG. 6C), the user selects one of the configurations of the ruler shown in FIGS. 7A-7C.

By way of example, the user can select the configuration shown in FIG. 7B. In another dialog box, the user indicates if the external reference data set, for example from a CT scan, is loaded from the PACS system or external storage media, e.g., DVD, flash drive or other suitable media.

The selected reference data set is loaded into a window similar to that shown for data set selection of the ruler, such as the display shown in FIG. 6B. The user selects the desired position in the volume using positioning aids, such as selection lines 48. The user also indicates which view is desired for the reference image, i.e., axial, sagittal, coronal or 3-D. Preferably, the user selects the same view for the reference image set and the ruler image set. e.g. axial view. However, mismatched views, and even mismatched anatomy (i.e. hand in the ruler image and knee in the reference set) can also be evaluated.

After the selection of the view and position of the reference data set, the GUI displays the reference image and the ruler image side by side. The user may also switch/swap the sides for the ruler and reference images using an additional button on the GUI, so that small differences in the display or the viewing angle do not affect the results.

In an adjustment step S960, the user manipulates indicator 66 on the slider bar or any other ruler control mechanism until the ruler image shows the desired result in terms of noise factor. On-screen instructions may display/illustrate/indicate/emphasize that the decision should be made based on the ability to diagnose disease features, which is not necessarily equivalent with the lowest noise image.

Once the selection is made, the GUI displays a numerical value associated with the selected ruler image, e.g., the noise factor or the relative change in noise in percent relative to the reference image. On leaving the setup screen, for example using control buttons 62 in FIG. 6B, the system prompts the user with the option to apply the selected noise setting to the AEC setup for the selected anatomy in a transfer value step S970. This workflow can then be repeated for different views or positions of the same volume data sets or for different anatomy.

According to an alternate embodiment of the present disclosure, a further customization instruction is provided. This allows one or more operators at a site to automatically reduce or increase dose from calculated settings based on noise factor effects. This feature can allow higher noise, for example, while helping to further reduce patient dose. Customizable noise factor adjustment may be enabled selectively according to an embodiment of the present disclosure. Thus, for example, some noise factor flexibility can be allowed for some limbs. For example, customization of exposure levels can be applied to wrists and to ankles, but not to knees.

According to an alternate embodiment, a lead operator/technician at a site can enter global adjustments to computed values, such as reducing exposure for all exams at a site by 10% from calculated exposure values. Global adjustments can be set up for all exams, or for specific types of exams, for example, such as for wrists but not for knees.

According to another alternate embodiment, there can be global operator instructions for examinations requiring low or high dose based on the contrast of the anatomy examined, for example.

The CBCT system itself may limit variability of exposure-related values to a narrow range, such as shown in the graph of FIG. 8. There may be fixed values for kVp and a small range of mAs values available on a particular system.

A computer program product may include one or more storage medium, for example; non-transient media, magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The methods described above may be described with reference to a flowchart. Describing the methods by reference to a flowchart enables one skilled in the art to develop such programs, firmware, or hardware, including such instructions to carry out the methods on suitable computers, executing the instructions from computer-readable media. Similarly, the methods performed by the service computer programs, firmware, or hardware are also composed of computer-executable instructions.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B." unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

In the following claims, the terms "first," "second," and "third," and the like, are used merely as labels, and are not intended to impose numerical requirements on their objects.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for setting an automatic exposure control in a volume radiographic imaging apparatus, the method comprising:

displaying a first image slice selected by an operator of the apparatus;

displaying a single second image slice adjacent to the first image slice, the displayed single second image slice selected from a series of second image slices stored in sequential order of decreasing or increasing noise factor, the displayed second image slice configured to be displayed in sequential order one-at-a-time backward or forward in the stored sequential order under control of the operator, the series of second image slices each stored in association with an imaging technique value; and in response to the operator choosing a currently displayed second image slice, automatically setting an x-ray exposure level of the automatic exposure control according to the imaging technique value stored in association with the chosen currently displayed second image slice.

2. The method of claim 1, further comprising automatically setting an exposure time product of the automatic exposure control.

3. The method of claim 2, further comprising reconstructing a volume image of an object using a series of projection images of the object acquired by the volume radiographic imaging apparatus using the automatically set automatic exposure control.

4. The method of claim 3, further comprising storing, in association with each of the series of projection images of the object, data relating to at least one of: a size of the object, a radiation dose of the automatically set automatic exposure control, and an x-ray technique associated with the automatically set automatic exposure control.

5. The method of claim 1, further comprising displaying the first image slice using a predetermined fixed reference noise factor.

6. The method of claim 1, further comprising fixing a noise level of the displayed first image slice at an operator selected noise level.

7. The method of claim 6, further comprising storing a plurality of reference images each having a different noise level, the plurality of reference images each accessible by the volume radiographic imaging apparatus for operator selection as the displayed first image slice.

8. A method for automatically setting an automatic exposure control of a volume radiographic imaging apparatus, the method comprising:
displaying a reference radiographic image in a first display window, the reference radiographic image selected by an operator of the radiographic imaging apparatus;
displaying a variable noise radiographic image in a second display window adjacent to the first display window, the variable noise radiographic image selected from a series of variable noise images stored in sequential order of decreasing or increasing noise level, the displayed variable noise radiographic image configured to be selected in sequential order backward or forward from the series of variable noise images under control of the operator, the series of variable noise images stored each stored in association with corresponding exposure data;
varying a noise level of the displayed variable noise radiographic image in response to the operator manipulating a user interface of the radiographic imaging apparatus; and
in response to the operator selecting one of the displayed variable noise radiographic images having a particular noise level, accessing the exposure data stored in association with the selected one of the variable noise radiographic images and automatically setting an x-ray exposure duration of the automatic exposure control according to the accessed exposure data.

9. A radiographic imaging system comprising:
a revolvable x-ray source adjustable to emit x-rays at a preselected energy level;
a revolvable detector configured to capture images of an object exposed by the revolvable x-ray source;
a display for displaying x-ray images;
an automatic exposure control; and
a library comprising a plurality of digitally stored x-ray images accessible by the system, the x-ray images digitally stored in a sequential order of increasing or decreasing noise level, the x-ray images each captured using x-rays emitted at a corresponding energy level, the library including corresponding technique data used to capture each x-ray image,
wherein the system is configured to sequentially display at least a subset of the digitally stored x-ray images in sequential order of increasing or decreasing noise level under control of an operator of the system, the system is configured to receive from the operator a selection of one of the sequentially displayed x-ray images, and
wherein the system is configured to automatically adjust an x-ray emission duration of the automatic exposure control according to the technique data corresponding to the operator selected one of the sequentially displayed x-ray images.

10. The system of claim 9, wherein the revolvable x-ray source is further adjustable to emit the x-rays for a preset exposure time, the plurality of digitally stored x-ray images each captured using x-rays emitted at a corresponding exposure time, the library including data representing the corresponding exposure time used to capture each x-ray image, and wherein the system is configured to automatically adjust the preset exposure time to match the corresponding exposure time used to capture the operator selected one of the sequentially displayed x-ray images.

\* \* \* \* \*